United States Patent
East et al.

(10) Patent No.: US 11,607,529 B2
(45) Date of Patent: Mar. 21, 2023

(54) FIXATION DEVICES FOR CATHETERS

(71) Applicant: ALCYONE THERAPEUTICS, INC., Lowell, MA (US)

(72) Inventors: Andrew East, Arlington, MA (US); Burt Raymond, Nashua, NH (US); Andre Carline Wood, Worchester, MA (US); Deep Arjun Singh, Cambridge, MA (US); Jonathan Freund, Woburn, MA (US); John L. Mcguire, Westborough, MA (US); Krishna Subramanian, Mechanicsville, VA (US); Matthew J. Lapinski, Lowell, MA (US); Megan Holmes, Cambridge, MA (US); Thomas T. Washburn, Lancaster, MA (US)

(73) Assignee: ALCYONE THERAPEUTICS, INC., Lowell, MA (US)

( * ) Notice: Subject to any disclaimer, the term of this patent is extended or adjusted under 35 U.S.C. 154(b) by 0 days.

(21) Appl. No.: 17/588,087

(22) Filed: Jan. 28, 2022

(65) Prior Publication Data
US 2022/0241559 A1 Aug. 4, 2022

Related U.S. Application Data

(60) Provisional application No. 63/143,377, filed on Jan. 29, 2021.

(51) Int. Cl.
*A61M 25/02* (2006.01)

(52) U.S. Cl.
CPC ....... *A61M 25/02* (2013.01); *A61M 2025/024* (2013.01); *A61M 2025/0286* (2013.01)

(58) Field of Classification Search
CPC ............ A61M 25/02; A61M 2025/024; A61M 2025/028; A61M 2039/1027; A61M 39/12; A61M 5/1418; A61M 5/1417; A61M 2025/0246; A61M 39/1011; A61M 39/10; A61M 39/284; A61M 2039/1066; A61M 2025/0253; A61M 39/28; A61M 2025/0293; A61B 17/08; A61B 17/083; A61B 17/122; A61B 17/1227; A61B 17/0487; A61B 2017/0488;
(Continued)

(56) References Cited

U.S. PATENT DOCUMENTS

| | | | |
|---|---|---|---|
| 4,631,056 A * | 12/1986 | Dye | A61M 39/1011 604/905 |
| 4,699,616 A | 10/1987 | Nowak et al. | |
| 4,971,272 A | 11/1990 | Gudridge et al. | |

(Continued)

FOREIGN PATENT DOCUMENTS

JP   2006305025 A   11/2006

OTHER PUBLICATIONS

International Application No. PCT/US2022/014437, International Search Report and Written Opinion, dated Jun. 6, 2022.

*Primary Examiner* — Adam Marcetich
(74) *Attorney, Agent, or Firm* — Marshall, Gerstein & Borun LLP

(57) ABSTRACT

Fixation devices are disclosed herein that can be used to secure to a catheter and to tissue. The fixation devices include a body having a bore extending therethrough to receive a catheter. The fixation devices can also include suture openings or grooves to secure the devices to tissue.

12 Claims, 26 Drawing Sheets

(58) Field of Classification Search
CPC ........ A61B 2017/0454; A61B 17/0401; A61B 17/128; A61B 2017/0414; A61B 90/90
See application file for complete search history.

(56) References Cited

U.S. PATENT DOCUMENTS

| | | | |
|---|---|---|---|
| 5,423,763 A | 6/1995 | Helland et al. | |
| 5,683,403 A | 11/1997 | Adams et al. | |
| 5,810,853 A * | 9/1998 | Yoon ................ | A61B 17/0487 606/232 |
| 6,113,572 A | 9/2000 | Gailey et al. | |
| 6,387,076 B1 * | 5/2002 | Landuyt .............. | A61M 25/02 604/174 |
| 6,488,664 B1 * | 12/2002 | Solomon ............. | F16L 33/035 602/17 |
| 8,126,569 B2 | 2/2012 | Rivard et al. | |
| 9,642,987 B2 | 5/2017 | Bierman et al. | |
| 9,717,885 B1 | 8/2017 | Narciso Martinez et al. | |
| 10,814,104 B2 | 10/2020 | Amon et al. | |
| 11,351,365 B1 * | 6/2022 | McKeag ............ | A61N 1/36071 |
| 2001/0011164 A1 | 8/2001 | Bierman | |
| 2006/0064159 A1 | 3/2006 | Porter et al. | |
| 2007/0088329 A1 * | 4/2007 | Bierman .............. | A61M 25/02 604/533 |
| 2007/0261214 A1 * | 11/2007 | Nerbonne .......... | A61M 39/284 24/326 |
| 2008/0319421 A1 * | 12/2008 | Bizup ................ | A61M 39/12 604/533 |
| 2011/0163533 A1 * | 7/2011 | Snyder .............. | F16L 33/035 285/88 |
| 2012/0227221 A1 * | 9/2012 | Whitaker ............ | F16B 2/10 29/525.08 |
| 2013/0184687 A1 * | 7/2013 | Clark ................ | A61M 39/10 604/533 |
| 2013/0218205 A1 * | 8/2013 | Stanley ............ | A61B 17/0401 606/232 |
| 2014/0060655 A1 * | 3/2014 | Ramos .............. | F16K 7/063 251/9 |
| 2014/0236198 A1 | 8/2014 | Goldfarb et al. | |
| 2014/0330247 A1 * | 11/2014 | Rosenberg .......... | A61M 25/02 604/506 |
| 2015/0038912 A1 | 2/2015 | Karim et al. | |
| 2015/0308598 A1 * | 10/2015 | Lewis ............... | A61M 39/1011 285/257 |
| 2016/0213371 A1 * | 7/2016 | Miraki .............. | A61B 17/0469 |
| 2017/0050786 A1 | 2/2017 | Kozminkse | |
| 2018/0064502 A1 * | 3/2018 | Shamir .............. | F16B 2/10 |
| 2018/0266600 A1 * | 9/2018 | Stankowski ........ | F16L 33/225 |
| 2019/0111244 A1 * | 4/2019 | Amon ............... | A61M 39/1011 |
| 2020/0108242 A1 * | 4/2020 | Stankowski ........ | A61M 39/12 |
| 2020/0254222 A1 | 8/2020 | Anand et al. | |

* cited by examiner

1

FIXATION DEVICES FOR CATHETERS

CROSS-REFERENCE TO RELATED APPLICATION

This application claims the priority benefit of U.S. Provisional Application No. 63/143,377, filed Jan. 29, 2021, which is hereby incorporated by reference in its entirety.

FIELD OF THE DISCLOSURE

The present disclosure generally relates to catheters and, more particularly, to fixation devices for catheters.

BACKGROUND

Applying sutures directly around an implantation opening for a catheter in the tissue of a patient can risk suture rupture, catheter lumen collapse, or even catheter tear, depending on the materials used for the catheter and the suture. These failures could, in turn, undesirably lead to catheter migration. For applications, such as intrathecal catheters, having long-term implantation and life, these risks may be further amplified.

SUMMARY

In accordance with a first aspect, a fixation device for a catheter is disclosed that includes a body defining a bore for reception of a catheter, a first body portion of the body having a first bore portion, and a second body portion of the body having a second bore portion, where the first and second body portions are movable with respect to one another from an open configuration allowing the catheter to be inserted at least partially into the bore and a closed configuration with the first and second portions secured together to thereby enclose a length of the catheter within the bore. In a further aspect, the body can further define one or more suture openings extending therethrough to secure the body to tissue.

According to some forms, the fixation device can include one or more of the following: the body can include one or more wings extending outwardly from the bore; the fixation device can include a snap fit connector configured to hold the first body portion and the second body portion in the closed configuration, which, in a further form, can be a dual stage snap fit connector; the first body portion and the second body portion can be configured to press-fit together in the closed configuration; the first body portion and the second body portion can be pivotably coupled together by a hinge; the first bore portion can include a recess defined in the first body portion and the second bore portion can include a projection of the second body portion configured to be inserted into the recess in the closed configuration to form the bore; the first body portion can include a tooth extending toward the second body portion adjacent to the first bore portion and the second body portion can include a tooth extending toward the first body portion adjacent to the second bore portion, where the teeth of the first and second body portions at least partially overlap in the open configuration and, in further forms, the teeth can include a stop to restrict pivoting of the first and second body portions away from one another; the first body portion and the second body portion can be separate components, which, in a further form, can include the second bore portion comprising a deformable projection of the second body portion and the first bore portion comprising a recess defined in the first body portion and a membrane having an inverted wedge configuration received within the cavity, where the deformable projection is configured to be inserted into the recess in the closed configuration to form the bore; or the bore can include one or more ribs that extend radially therein to clamp on the catheter.

According to some forms, the first and second body portions can each include first and second outwardly oriented openings providing access to the first and second bore portions, respectively, and the first and second outwardly oriented openings can be aligned with the first and second body portions in the open configuration and radially offset from one another with the first and second body portions in the closed configuration. In a further form, the first and second body portions can each include a tubular portion and a plate portion, where the tubular portions define the first and second outwardly oriented openings and are rotatably coupled together in a hinge configuration to pivot the plate portions together in the closed configuration.

According to some forms, the first body portion can include a tubular projection with the first bore portion extending longitudinally therethrough and an annular groove extending around the tubular projection and the second body portion can include an annular member having an inwardly extending lip, where the second body portion is configured to fit around the tubular projection with the lip disposed within the annular groove. In a further form, the annular member can have a tapered configuration.

According to some forms, the first and second body portions can be elongate members having curved distal ends providing the first and second bore portions, where the elongate members are pivotably coupled together and biased to the closed configuration with the curved distal ends overlapping one another to trap the catheter therebetween.

In accordance with a second aspect, a fixation device for a catheter is described that includes a body defining a bore and an opening extending longitudinally along the bore and providing access thereto, and a securing member configured to secure to the body and extend across the opening to enclose a length of the catheter in the bore.

According to some forms, the body can include a cavity having portions aligned transversely across the bore offset from a center thereof and the securing member can be a fastener having barbs extending outwardly from a side thereof, where the fastener is configured to be inserted into the cavity after the catheter is placed inside the bore with the barbs facing away from the catheter to thereby enclose the catheter within the bore.

According to some forms, the body can include a base having an array of suture openings extending therethrough on opposite sides of the bore and the securing member can be one or more sutures threaded through the array of openings, where the one or more sutures have one or more portions extending over the opening. In further forms, the one or more sutures can be disposed in an X-shaped configuration; the body can define a central plug with the bore including a circular path extending around the central plug, such that the catheter is wrapped around the central plug when inserted into the bore; and/or the body can be at least partially deformable, such that edges of the body defining at least a portion of the opening can be resiliently flexed away from one another to allow the catheter to be inserted into the bore.

According to some forms, the body can have a tubular configuration with a longitudinal slit providing the opening to access the bore and the securing member can be one or more sutures wrapped around the body and extending over the opening to enclose the catheter within the bore. In further forms, the body can include grooves extending along an outside thereof in a spiral configuration to receive the one or more sutures therein and/or the fixation device can include a material disposed within the body extending around the bore to engage the catheter.

In accordance with a third aspect, a fixation device for a catheter is described that includes a body having a distal end with a curved configuration extending back over the body, the curved configuration defining a bore for reception of a catheter therein, and an edge of the distal end being spaced from the body to define a longitudinal opening to the bore. The longitudinal opening has a width smaller than an outer diameter of the catheter, such that the catheter must be resiliently deformed to fit through the longitudinal opening to dispose the catheter within the bore.

According to some forms, the fixation device can include one or more of the following: an inner diameter of the bore can be smaller than an outer diameter of the catheter, such that the distal end applies a compressive force on the catheter; the body can include a relatively hard material extending along an interior surface of the distal end; the body can include a relatively hard material embedded within the distal end; or the body can include one or more suture openings extending therethrough.

According to a fourth aspect, a fixation device for a catheter is described that includes a body having a tubular configuration defining a bore for reception of a catheter, the body having a proximal end and a distal end, and an opening to the bore including a loading portion extending at least partially along the proximal end of the body from an end edge of the body to a side of the body and a spiral portion extending around the distal end of the body. The opening is configured to allow a catheter to be partially inserted into the bore through the loading portion and the distal end is configured to be rotated around the catheter to load the catheter through the spiral portion to fully dispose a length of the catheter within the bore.

According to some forms, the distal end of the body can have a reduced inner diameter relative to the proximal end of the body and the reduced inner diameter can be smaller than an outer diameter of the catheter, such that the distal end of the body applies a compressive force to the catheter when the catheter is loaded into the bore; and/or the body can include one or more tabs extending outwardly from the proximal portion, the distal portion, or a combination thereof, where the one or more tabs define suture openings extending therethrough.

DETAILED DESCRIPTION

Figure 1:
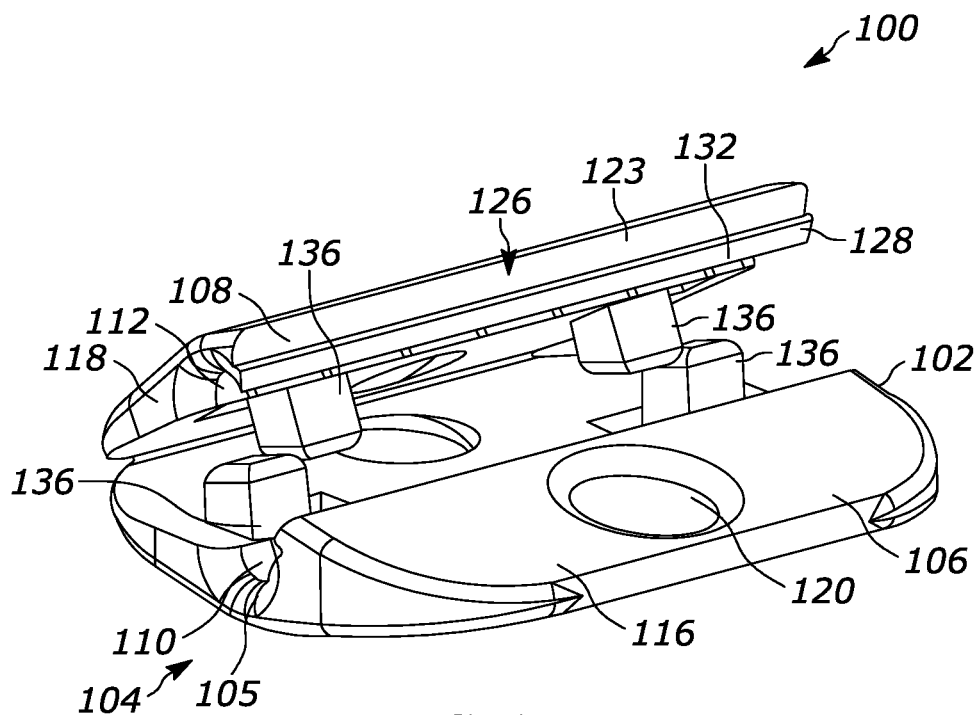
FIG. 1 is a perspective view of a first example fixation device for a catheter in a first form showing first and second body portions in an open configuration.
Figure 2:
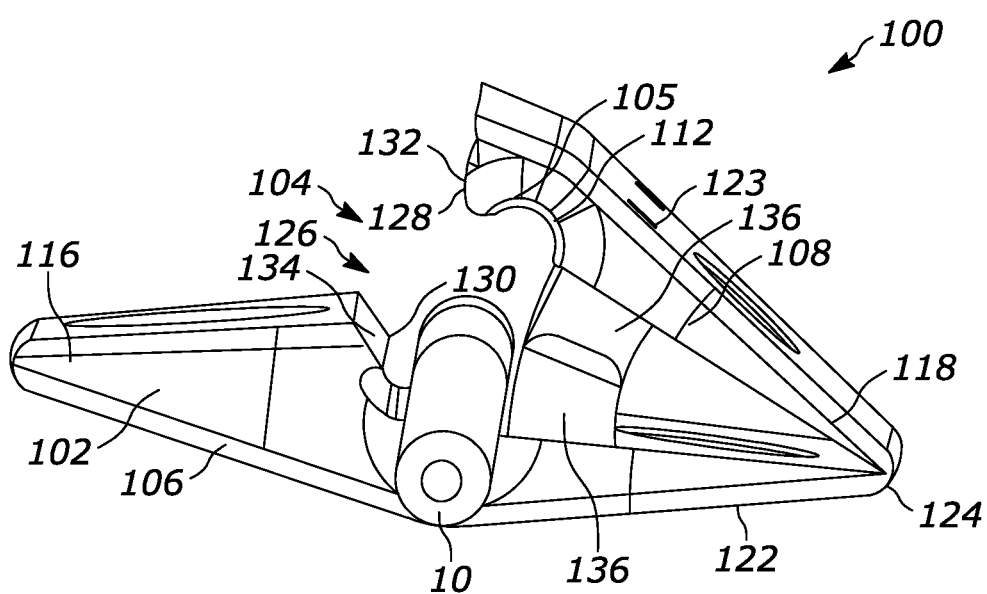
FIG. 2 is a perspective view of the fixation device of FIG. 1 showing a catheter inserted therein with the first and second body portions in the open configuration.
Figure 3:
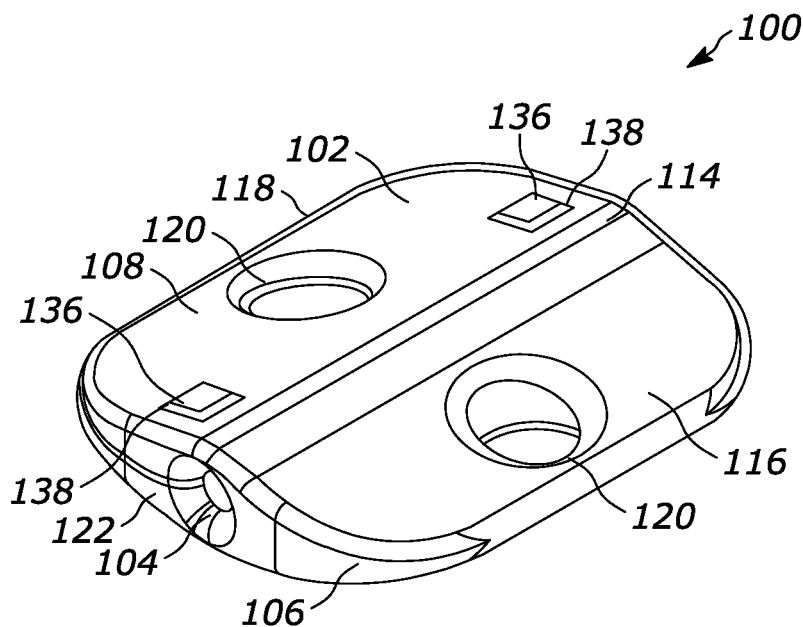
FIG. 3 is a perspective view of the fixation device of FIG. 1 showing the first and second body portions in a closed configuration.
Figure 4:
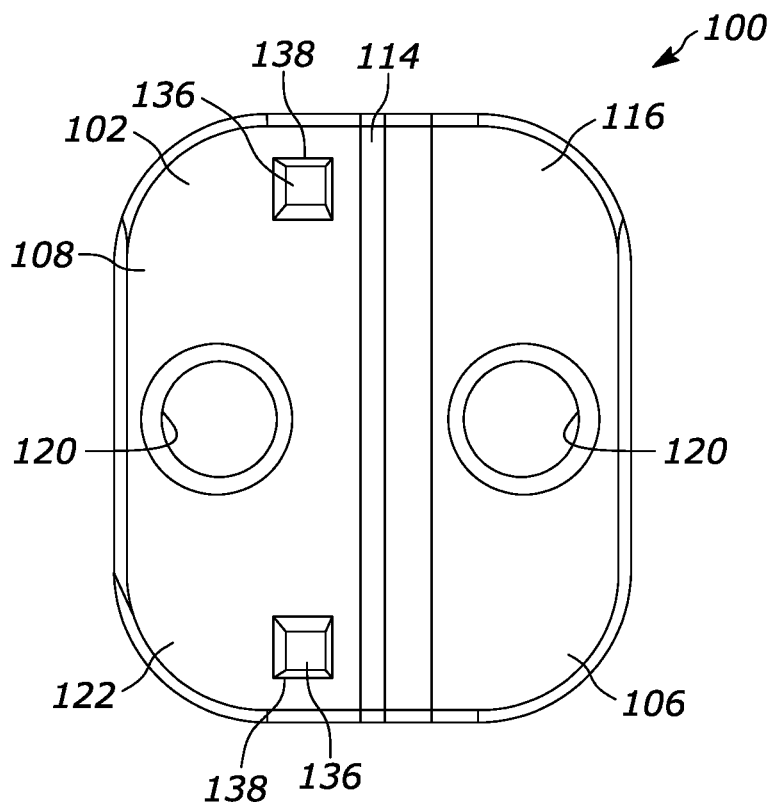
FIG. 4 is a top plan view of the fixation device of FIG. 1.
Figure 5:
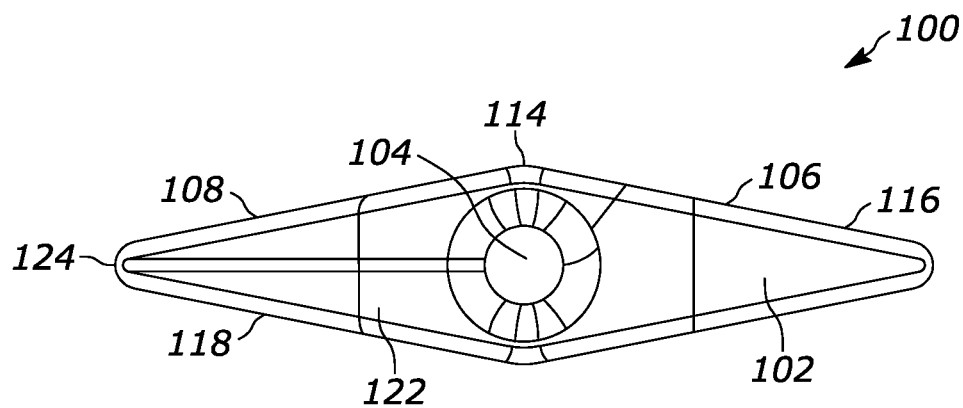
FIG. 5 is a front elevational view of the fixation device of FIG. 1.
Figure 6:
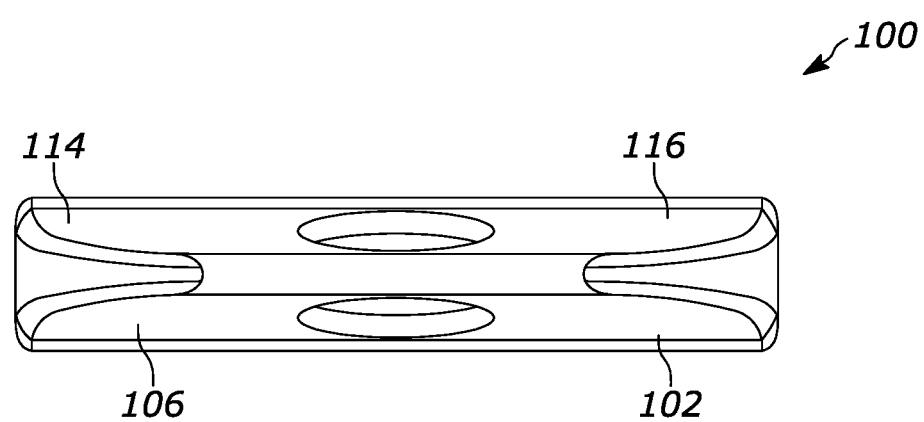
FIG. 6 is a side elevational view of the fixation device of FIG. 1.
Figure 7:
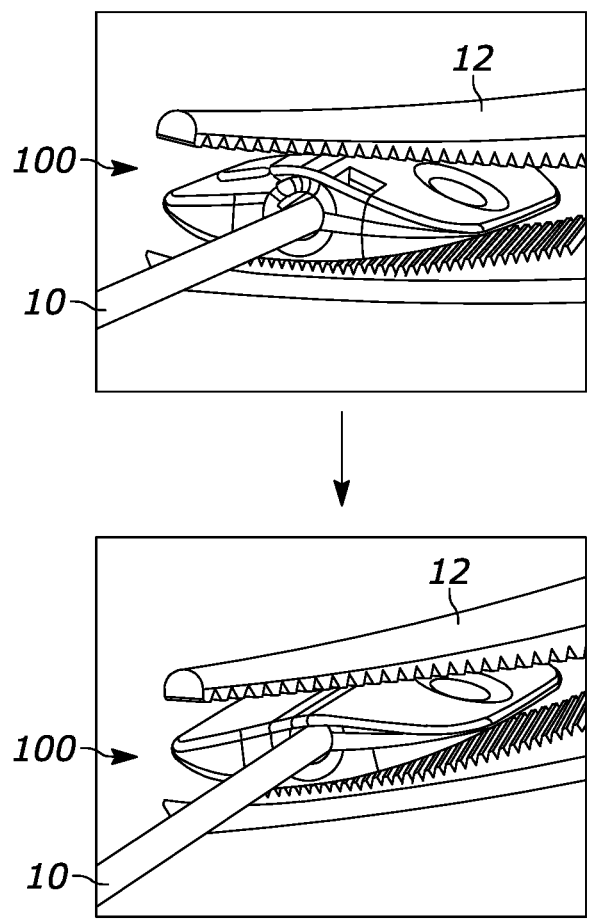
FIG. 7 is a perspective view of the fixation device of FIG. 1 showing a process of securing the fixation device to a catheter with forceps.
Figure 8:
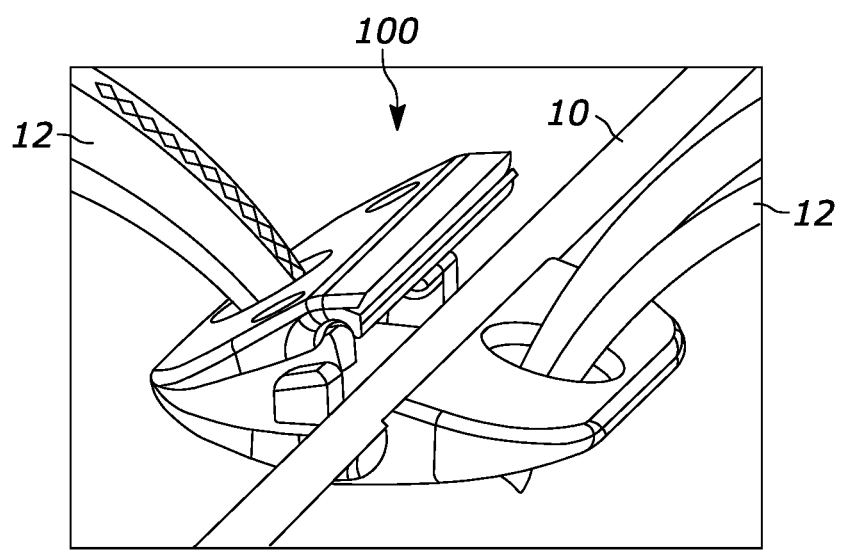
FIG. 8 is a perspective view of the fixation device of FIG. 1 showing the first and second body portions moved to an open configuration by forceps.
Figure 9:
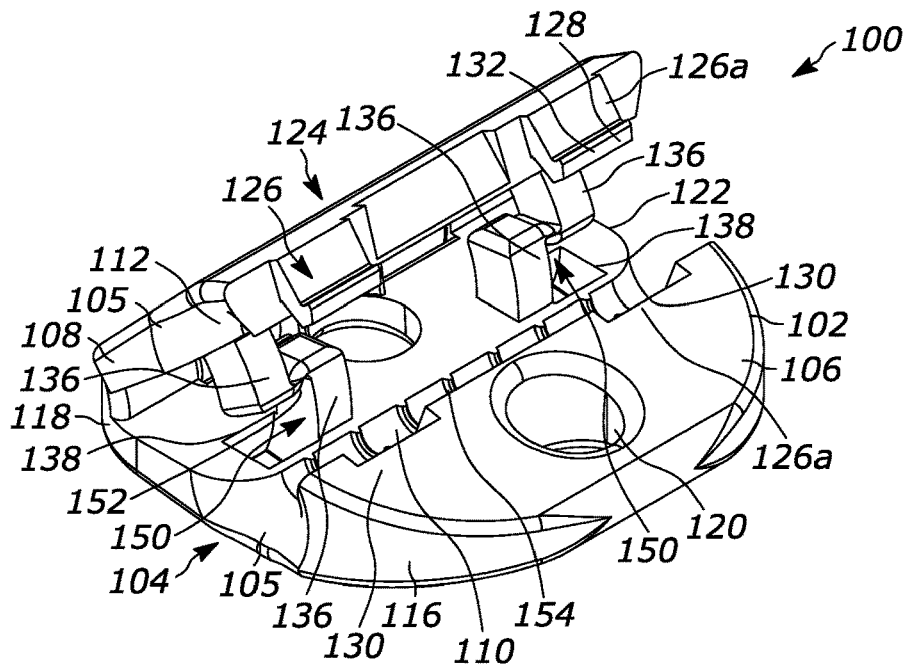
FIG. 9 is a perspective view of the first example fixation device for a catheter in a second form showing first and second body portions in an open configuration.
Figure 10:
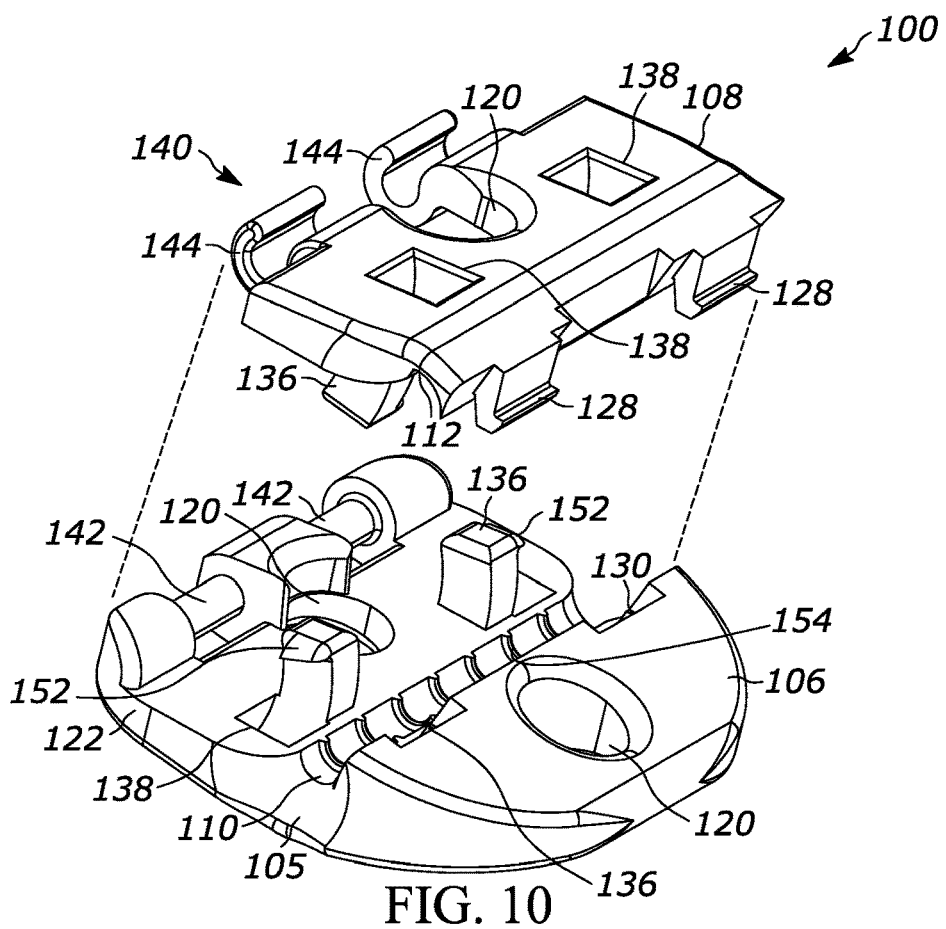
FIG. 10 is an exploded view of the fixation device of FIG. 9.
Figure 11:
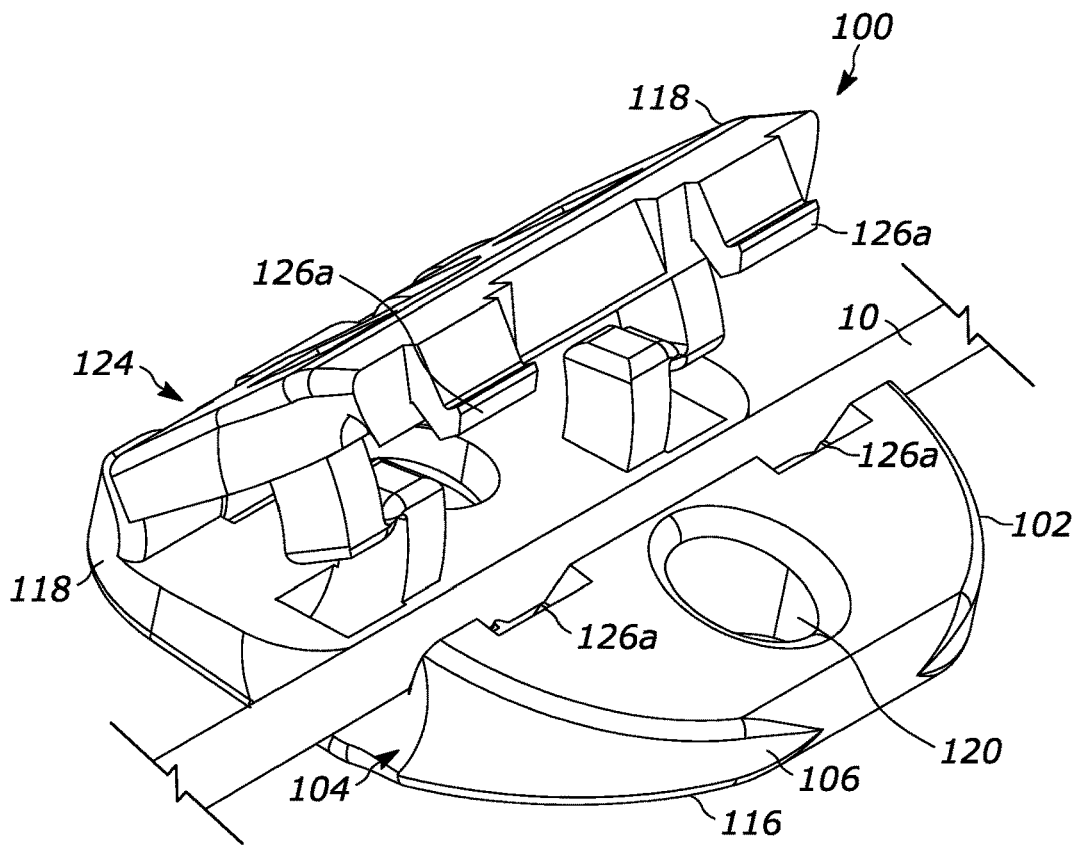
FIG. 11 is a perspective view of the fixation device of FIG. 9 showing a catheter inserted therein with the first and second body portions in the open configuration.
Figure 12:
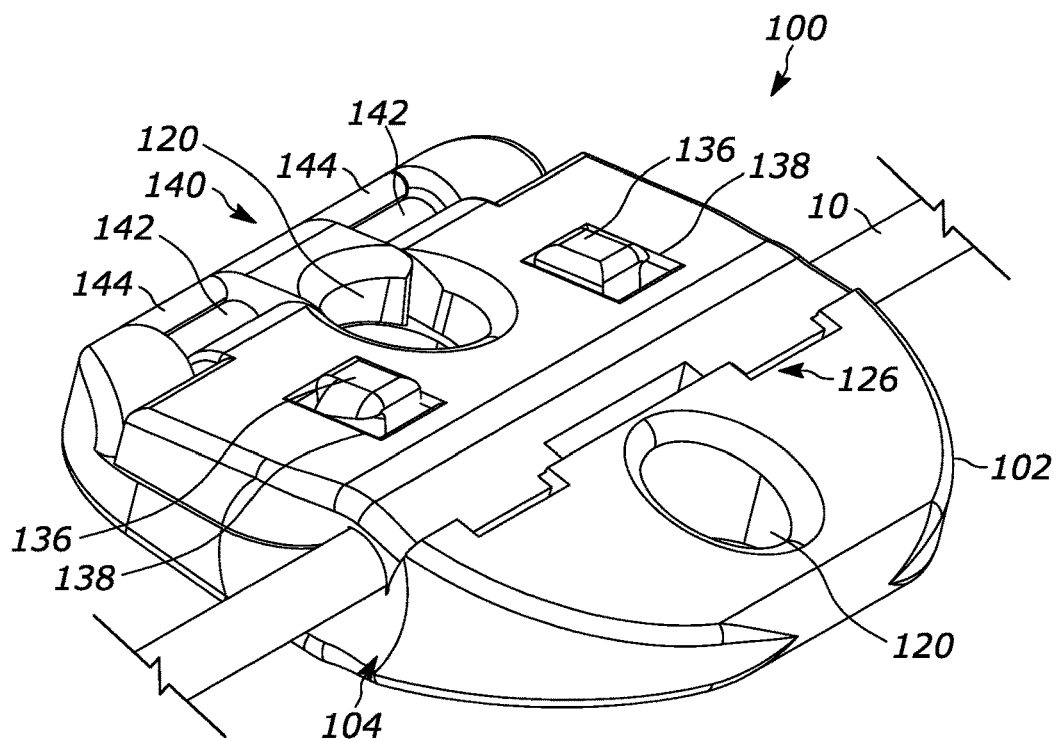
FIG. 12 is a perspective view of the fixation device of FIG. 9 showing the first and second body portions in a closed configuration.
Figure 13:
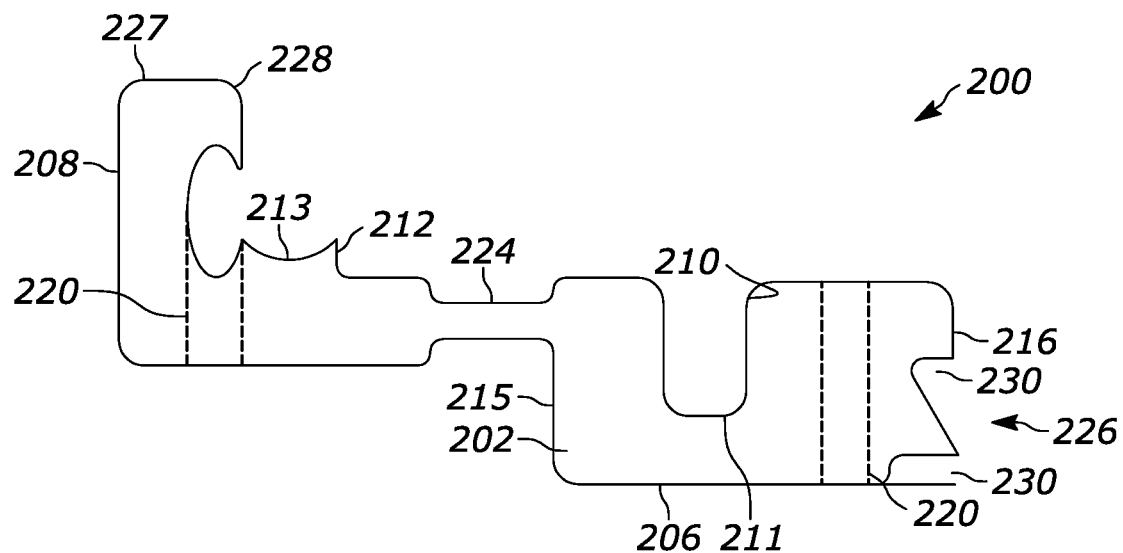
FIG. 13 is a front elevational view of a second example fixation device for a catheter showing first and second body portions in an open configuration.
Figure 14:
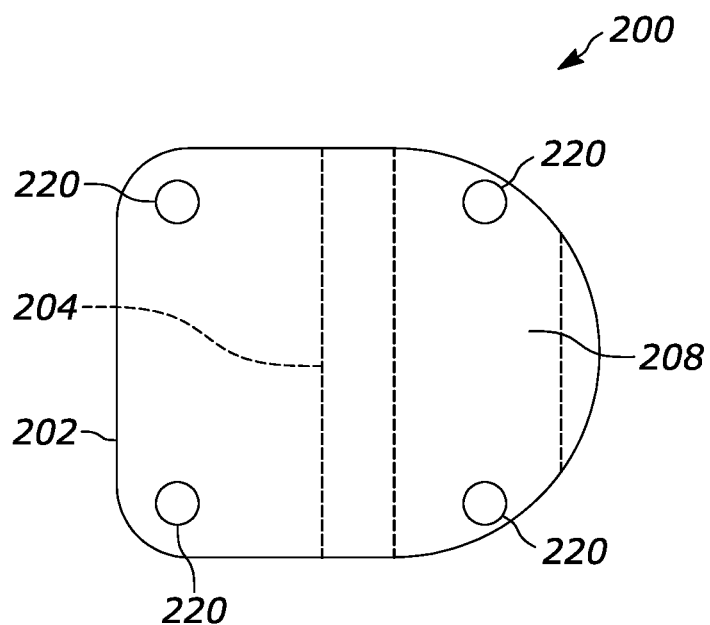
FIG. 14 is a top plan view of the fixation device of FIG. 13.
Figure 15:
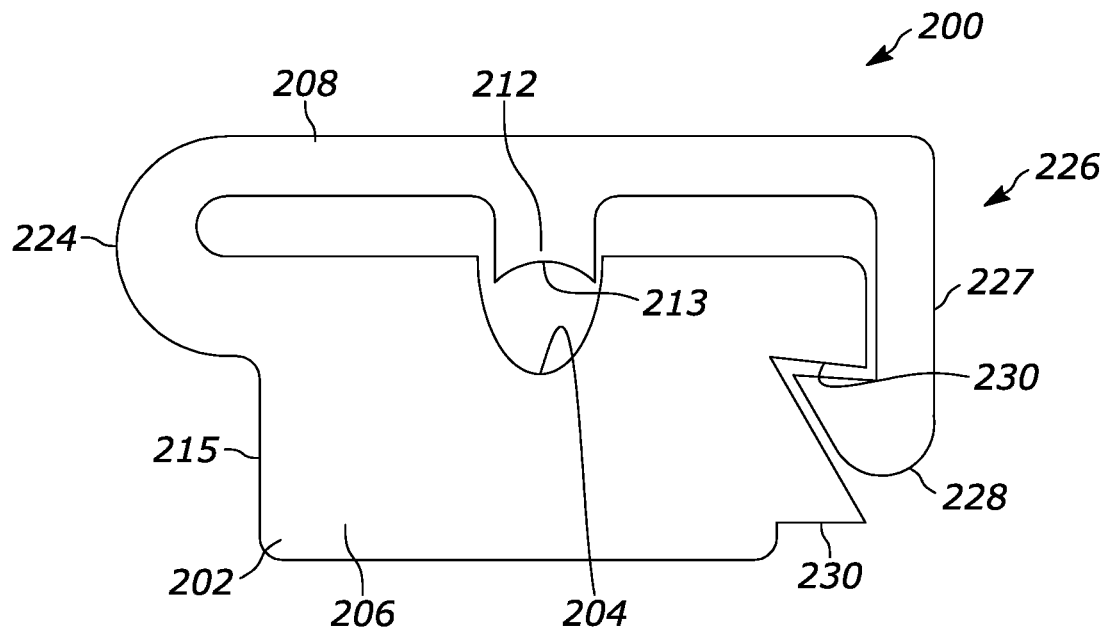
FIG. 15 is a front plan view of the fixation device of FIG. 13 showing the first and second body portions in a first stage of a dual stage connector.
Figure 16:
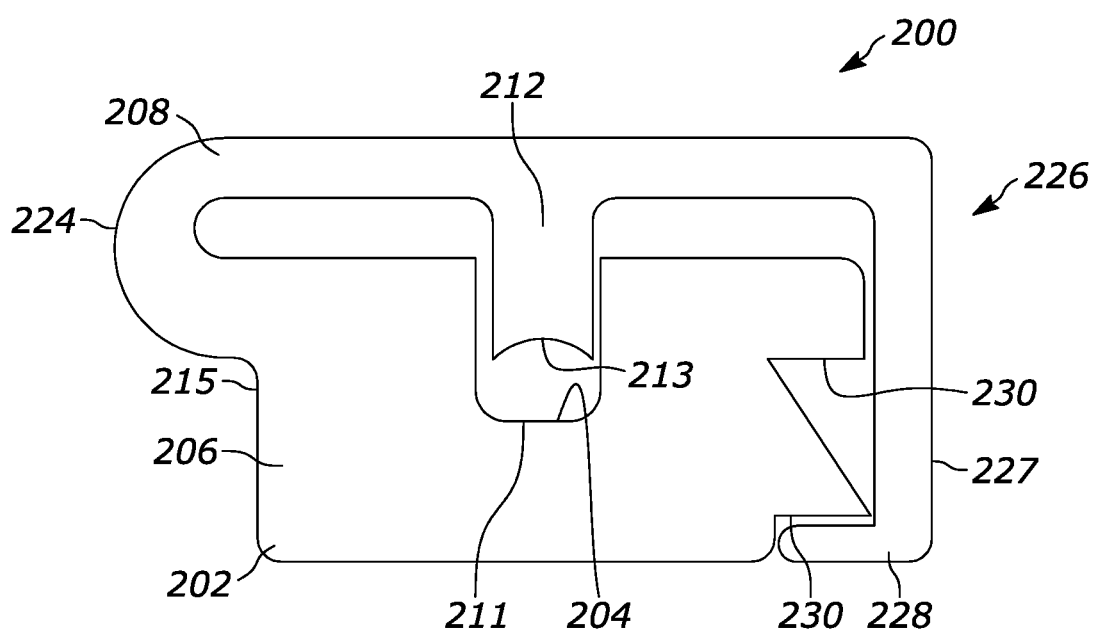
FIG. 16 is a front elevational view of the fixation device of FIG. 13 showing the first and second body portions in a second stage of a dual stage connector.

Fixation devices, which can include fixation tabs, suture wings, or anchoring wings, are disclosed herein that can be used to secure to a catheter and, optionally, secure a catheter in place with the use of sutures. The fixation devices can aid in preventing catheter migration or dislodgement from an implantation site. For intrathecal applications, the fixation devices disclosed herein can be implantable for relatively long-term periods to secure or anchor the catheter to the fascia of the patient after the catheter has been implanted in the intrathecal space.

The fixation devices disclosed herein can advantageously provide one or more of the following aspects: provide a minimum retention force of 2N and a maximum retention force of 18N; can have a minimal profile with a small height to width ratio; be sized and configured to minimize tissue erosion and ease procedure issues; be configured to engage and retain a catheter without damaging the catheter; be configured to not cause greater than a 10% reduction in flow through the catheter after being secured to the catheter; one or more portions of the fixation devices can be radiopaque and/or be made from biocompatible materials suitable for long-term implantation; the components providing retention force on the catheter and/or other design features of the fixation device can be suitable for the life of the device; or can be intuitive and easy to use and apply.

A first example fixation device 100 for a catheter 10 is shown in FIGS. 1-12. The fixation device 100 includes a body 102 that defines a bore 104 for reception of the catheter 10. In this form, the body 102 includes a first body portion 106 and a second body portion 108 that are movable with respect to one another from an open configuration where the catheter 10 can be placed at least partially within the bore 104 and a closed configuration where a length of the catheter 10 is enclosed and retained within the bore 104. If desired, the bore 104 can include radiused ends 105 which allow the catheter 10 to flex or travel in directions angled from a longitudinal axis of the body 102.

As shown, the first body portion 106 includes a first bore portion 110 and the second body portion 108 includes a second bore portion 112, where the first and second bore portions 110, 112 cooperate to form the bore 104. In the illustrated form, the first and second bore portions 110, 112 are half-cylinder cavities extending along an entire longitudinal length of the body 102.

As shown, the body 102 can include a center portion 114 through which the bore 104 extends and first and second wings 116, 118 extending outwardly from the center portion 114. In the form shown in FIGS. 1-8, the body 102 has a diamond-shaped cross-sectional profile in a plane transverse to the longitudinal length thereof with the bore 104 positioned generally centrally corresponding to the center portion 114 which has a raised configuration and the first and second wings 116, 118 which taper as they extend outwardly from the raised center portion 114. If desired, the body 102 can further define one or more suture openings 120, such as one extending through each wing 116, 118, as shown, to secure the fixation device 100 to tissue. By having suture openings 120 on both sides of the bore 104, sutures will securely hold a catheter 10 in a desired location along the tissue of a patient.

In the illustrated form, the first body portion 106 can include the first wing 116, the first bore portion 110, and a lower half 122 of the second wing 118, while the second body portion 108 can include an upper half 123 of the second wing 118 and the second bore portion 112. As shown, the first and second body portions 106, 108 are pivotably connected together along an outer edge 124 of the second wing 118, such that the first and second bore portions 110, 112 can be moved towards and away from one another. Accordingly, the fixation device 100 of this form advantageously provides side loading of the catheter 10 into the bore 104, which can be placed by hand or tool.

In one form shown in FIGS. 1-8, the first and second body portions 106, 108 can be a single-piece component and the outer edge 124 can be a living hinge connecting the body portions 106, 108. In a second form, shown in FIGS. 9-12, the first and second body portions 106, 108 can be coupled by a hinge mechanism 140. For example, the body portions 106, 108 can be pivotable with respect to one another about one or more rods 142, which in the illustrated form are formed by the first body portion 106. The second body portion 108 can then include one or more hook or loop connectors 144 configured to pivotably mount to the rod 142. As shown, the rods 142 and hook connectors 144 can have a generally equal, e.g., within 0-3 mm, longitudinal length to ensure that components of the body portions 106, 108, described in more detail below, are aligned for connection to a catheter 10. Of course, other suitable hinges or configurations can alternatively be utilized, including a separate rod component extending within hinge components of the body portions.

As shown, the body portions 106, 108 secure together with a connector 126. By one approach, the connector 126 can be a snap-fit connector provided by interlocking jaws 128, 130 of the first and second body portions 106, 108. The jaws 128, 130 are engageable by pivoting the body portions 106, 108 toward one another about the hinge 124, which causes angled surfaces 132, 134 of the first and second body portions 106, 108 to engage and slide along one another until a portion of the body portions 106, 108 deform and allow the jaws 128, 130 to pass one another. Thereafter, the jaws 128, 130 can interlock and prevent the body portions 106, 108 from pivoting away from one another. With this configuration, the fixation device 100 can be a single-piece component with a single action to snap to the closed configuration. This configuration can be utilized to provide a high retention force on the catheter 10, while also providing easy placement with a smooth and atraumatic body 102. The connector 126 can be a one-piece component that extends some or all of the length of the body portions 106, 108 as shown in FIGS. 1-8 or can include discrete connector portions 126a spaced from one another along a longitudinal length of the body portions 106, 108 as shown in FIGS. 9-12. Additionally, the fixation device 100 can be made from a single material, such as polyetheretherketone ("PEEK").

To aid in placement and retention of the catheter 10, the first and/or second body portions 106, 108 can include one or more teeth 136 that extend toward the other body portion 106, 108 adjacent to the bore 104. For example, the teeth 136 can extend outwardly from an edge of the first and/or second bore portions 110, 112 or closely (e.g., between 1-5 mm) adjacent thereto. The teeth 136 can have linear edges or can have a curved configuration, as shown in the figures. For example, the teeth 136 can have a curvature that is complementary to a curvature that the body portions 106, 108 travel along as they are pivoted with respect to one another.

This configuration provides a backstop for the catheter 10 opposite the open side of the bore 104 when the catheter 10 is being inserted into the bore 104 with the body portions 106, 108 in the open configuration. Further, the body portion 106, 108 opposite the teeth 136 can include a recess or opening 138 aligned with the teeth 136, where the recess 138 receives the tooth 136 when the body portions 106, 108 are pivoted to the closed configuration.

If desired, the first and second body portions 106, 108 can each include teeth 136 with travel paths adjacent to one another, such that sides of the teeth abut or are closely spaced from one another. This configuration allows the body portions 106, 108 to be pivoted further away from one another while still providing an unbroken backstop for insertion of the catheter 10 into the bore 104. In one form, the body portions 106, 108 can include two pairs of teeth 136 adjacent to ends of the bore 104 to provide two backstop locations. The pairs of teeth 136 can be provided in a hippo-tooth format with the teeth 136 of the second body portion 108 being disposed inwardly of the teeth 136 of the first body portion 106. Of course, the opposite format or a repeating pattern could alternatively be utilized. In some forms, the teeth 136 and recesses 138 can be configured to provide additional clamping strength, such as by press-fit, snap-fit, etc.

In one example, as shown in FIGS. 9-12, adjacent teeth 136 of the body portions 106, 108 can include a stop 150 that restricts the body portions 106, 108 from pivoting further away from one another. The stop 150 can include tabs 152 that extend outwardly from the teeth 136 into the travel path of one another. With this configuration, the tabs 152 engage one another in an open configuration that allows the catheter 10 to be inserted into the bore 104, but prevent the body portions 106, 108 from pivoting to a position where the teeth 136 do not overlap. In the illustrated example, the interior teeth 136 of the first body portion 106 include outwardly extending lips 152 and the exterior teeth 136 of the second body portion 108 include inwardly extending lips 152. Of course, other configurations are possible.

To provide further clamping force on the catheter 10, one or both of the bore portions 110, 112 can include ribs 154 that extend into the bore 104 to engage the catheter 10. In the illustrated form, device 100 includes a plurality of ribs 154 that extend radially around the bore 104 and are longitudinally spaced from one another. It should be understood, however, that other configurations, such as spiral and the like, can alternatively be utilized.

With this configuration, the fixation device 100 can be placed on the catheter 10 with a side loading function when the first and second body portions 106, 108 are in the open configuration. A user can then clamp down slightly on the body 102, such as with forceps 12, to contain the catheter 10 within the bore 104 without interlocking the jaws 128, 130. This allows the user to slide the device 100 axially along the catheter 10 to a desired position. Then, the user can apply increased clamping pressure until the jaws 128, 130 snap fit together, which engages the catheter 10 and secures the fixation device 100 in position along the catheter 10. If removal is desired, forceps 12 can be inserted into the suture openings 120 to crack open the body 102 by overcoming the latch strength of the jaws 128, 130. These configurations advantageously provide at least up to three controls for compression of the catheter 10 within the bore 104: (1) the diameter/height of the ribs 154 within the bore 104; (2) the number of ribs 154 in the bore 104; and (3) the diameter of the bore 104 corresponding to the jaws 128, 130 interlocking to a closed position.

A second example fixation device 200 for a catheter 10 is shown in FIGS. 13-16. The fixation device 200 includes a body 202 that defines a bore 204 for reception of the catheter 10. In this form, the body 202 includes a first body portion or base 206 and a second body portion or cover 208 that are movable with respect to one another from an open configuration where the catheter 10 can be placed at least partially within the bore 204 and a closed configuration where a length of the catheter 10 is enclosed and retained within the bore 204. If desired, the bore 204 can include radiused ends (not shown) which allow the catheter 10 to flex or travel in directions angled from a longitudinal axis of the body 202. In one example, the body 202 can be a clamshell housing with the body portions 206, 208 pivotably coupled together.

As shown, the first body portion 206 includes a first bore portion 210 and the second body portion 208 includes a second bore portion 212, where the first and second bore portions 210, 212 cooperate to form the bore 204. In the illustrated form, the first bore portion 210 is a channel or recess having a depth greater than or equal to a diameter of the catheter 10 with a concave bottom surface 211 that extends a longitudinal length of the body 202 and the second bore portion 212 is a projection or wall that is sized to fit within the channel of the first bore portion 210. As shown, an end surface 213 of the wall 212 has a concave shape, such that the bottom surface 211 and end surface 213 combine to form the cylindrical bore 204 when the wall 212 is inserted into the channel 210. The diameter of the channel 210 can be smaller than an outer diameter of the catheter 10, such that the catheter 10 can be press fit into the channel 210. Alternatively, the diameter of the channel 210 can equal to or slightly larger than the outer diameter of the catheter 10, such that the catheter 10 can be slid within the channel 210 to position the fixation device 200 at a desired location along the catheter 10.

As shown, the body portions 206, 208 are coupled together on a first side 215 of the body 202 by a flexible tether 224 that allows the body portions 206, 208 to pivot with respect to one another to thereby insert the wall 212 into the channel 210 after the catheter 10 has been placed therein. For example, the body portions 206, 208 could be pivotably coupled together by a hinge, such a living hinge. Advantageously, a second, opposite side 216 of the body 202 can include a connector 226 to secure the body portions 206, 208 in the closed configuration to thereby enclose the length of the catheter 10 in the device 200. By one approach, the connector 226 can be a snap-fit connector provided by a skirt 227 and lip 228 of the second body portion 208 and a ledge or recess 230 of the first body portion 206 that cooperate to hold the body portions 206, 208 in the closed configuration. If desired, the first body portion 206 can include two recesses 230 spaced from one another along a height thereof so that the connector 226 can be a dual-stage snap fit. The top recess 230 allows for a loose connection between the body portions 206, 208 where the catheter 10 can be enclosed within the bore 204 without the surfaces 211, 213 tightly engaging the catheter 10 such that the fixation device 200 can be slid along the catheter 10 to position it at a desired location. Thereafter, a user can squeeze the body portions 206, 208 together, such as with a forceps, to interlock the lip 228 and the second, lower recess 230 to thereby engage the catheter 10 with the surfaces 211, 213 and restrict movement of the catheter 10 relative to the fixation device 200.

If desired, the body 202 can further define one or more suture openings 220 to secure the fixation device 200 to tissue. For example, the body 202 can include one suture opening 220 on either side of the bore 204 or four suture openings 220 extending through corners of the body 202. The suture openings 220 can extend through the first body portion 206 and, if aligned with the second body portion 208, through the second body portion 208. By having suture openings 220 on both sides of the bore 204, sutures will securely hold a catheter 10 in a desired location along the tissue of a patient.

With this configuration, the fixation device 200 can be a single-piece component with a single action to snap to the closed configuration. This configuration can be utilized to provide a high retention force on the catheter 10, while also providing easy placement with a smooth and atraumatic body 202. Additionally, the fixation device 200 can be made from a single material.

Figure 17:
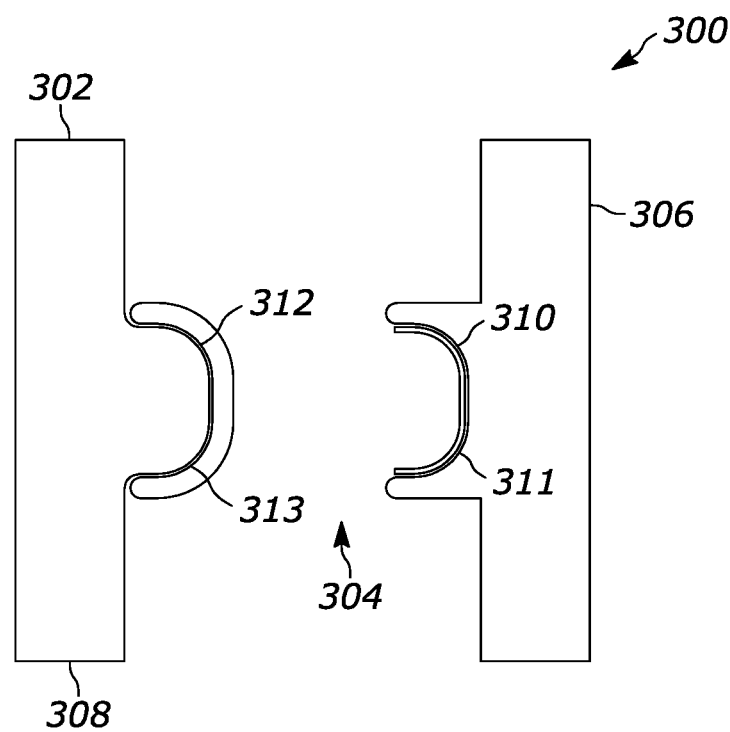
FIG. 17 is an exploded view of a third example fixation device for a catheter showing first and second body portions in an open configuration.
Figure 18:
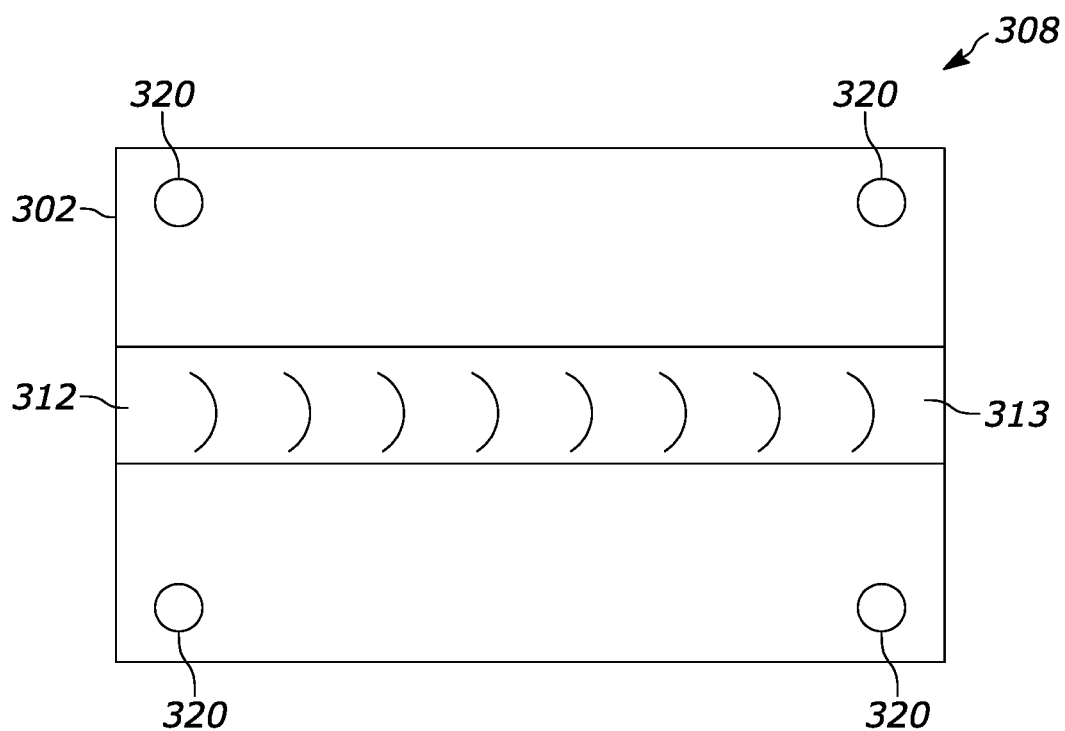
FIG. 18 is a top plan view of the first body portion of the fixation device of FIG. 17.
Figure 19:
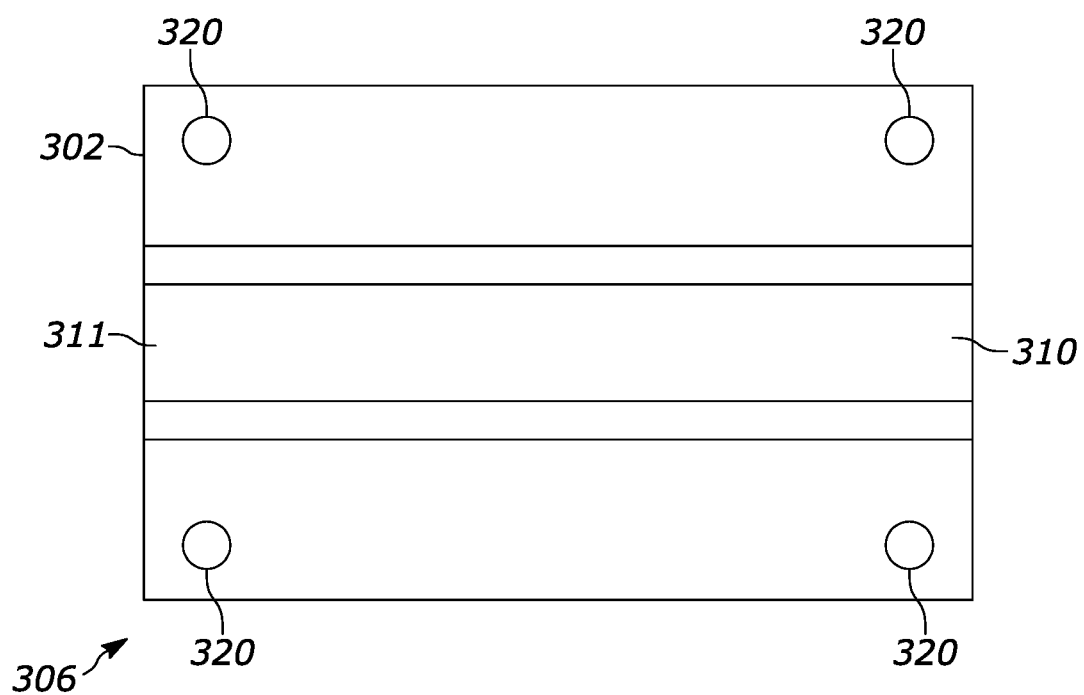
FIG. 19 is a top plan view of the second body portion of the fixation device of FIG. 17.

A third example fixation device 300 for a catheter 10 is shown in FIGS. 17-19. The fixation device 300 includes a body 302 that defines a bore 304 for reception of the catheter 10. In this form, the body 302 includes a first body portion or base 306 and a second body portion or cover 308 that are separate and engagable from an open configuration where the catheter 10 can be placed at least partially within the bore 304 and a closed configuration where a length of the catheter 10 is enclosed and retained within the bore 304. If desired, the bore 304 can include radiused ends (not shown) which allow the catheter 10 to flex or travel in directions angled from a longitudinal axis of the body 302.

As shown, the first body portion 306 includes a first bore portion 310 and the second body portion 308 includes a second bore portion 312, where the first and second bore portions 310, 312 cooperate to form the bore 304. In the illustrated form, the first bore portion 310 is a channel or recess having a depth greater than or equal to a diameter of the catheter 10 with a concave bottom surface 311 that extends a longitudinal length of the body 302 and the second bore portion 312 is a projection or wall that is sized to fit within the channel of the first bore portion 310. The channel 310 can be formed in an upstanding wall as shown in FIG. 17 or can be recessed into a generally planar surface. As shown, an end surface 313 of the wall 312 has a convex shape configured to at least partially deform around the catheter 10, when the body portions 306, 308 are secured together with the catheter 10 in the bore 304. The bottom surface 311 and end surface 313 combine to form the bore 304 when the wall 312 is inserted into the channel 310. By one approach, the body portions 306, 308 can be made from a homogenous material that is either a thermoplastic or elastomeric material, or two separate materials.

As shown, the body portions 306, 308 are separate components that secure together when joined. In one form, the channel 310 and wall 312 can be sized to press-fit together, such that friction holds the body 302 in the closed configuration. In another form, the body portions 306, 308 can include a snap-fit connector to secure the body portions 306, 308 in the closed configuration to thereby enclose the length of the catheter 10 in the device 300.

If desired, the body 302 can further define one or more suture openings 320 to secure the fixation device 300 to tissue. For example, the body 302 can include one suture opening 320 on either side of the bore 304 or four suture openings 320 extending through corners of the body 302. The suture openings 320 can extend through the first body portion 306 and, if aligned with the second body portion 308, through the second body portion 308. By having suture openings 320 on both sides of the bore 304, sutures will securely hold a catheter 10 in a desired location along the tissue of a patient. Further, with forms having the suture openings 320 extending through both the body portions 306, 308, the sutures can aid in holding the body portions 306, 308 in the closed configuration.

In some forms, the body 302 can be made from or have the bottom surface 311 and/or end surface 313 coated or layered with a similar or identical material to the catheter 10. This configuration can increase the coefficient of friction between the device 300 and the catheter 10, which determines the retention force on the catheter 10.

Figure 20:
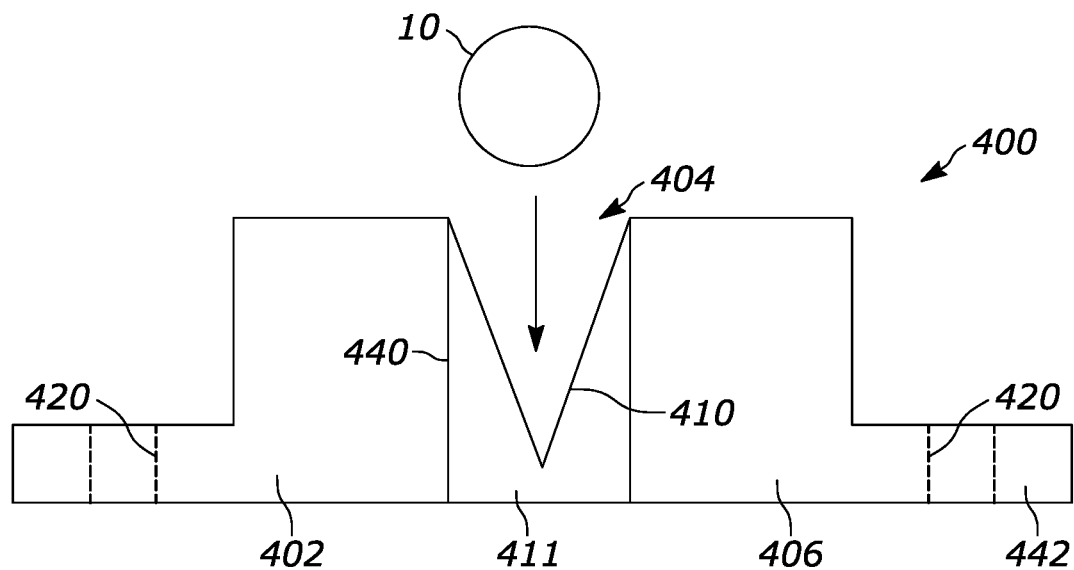
FIG. 20 is a front elevational view of a fourth example fixation device for a catheter showing a catheter being loaded into a recess defined by a base of the fixation device.
Figure 21:
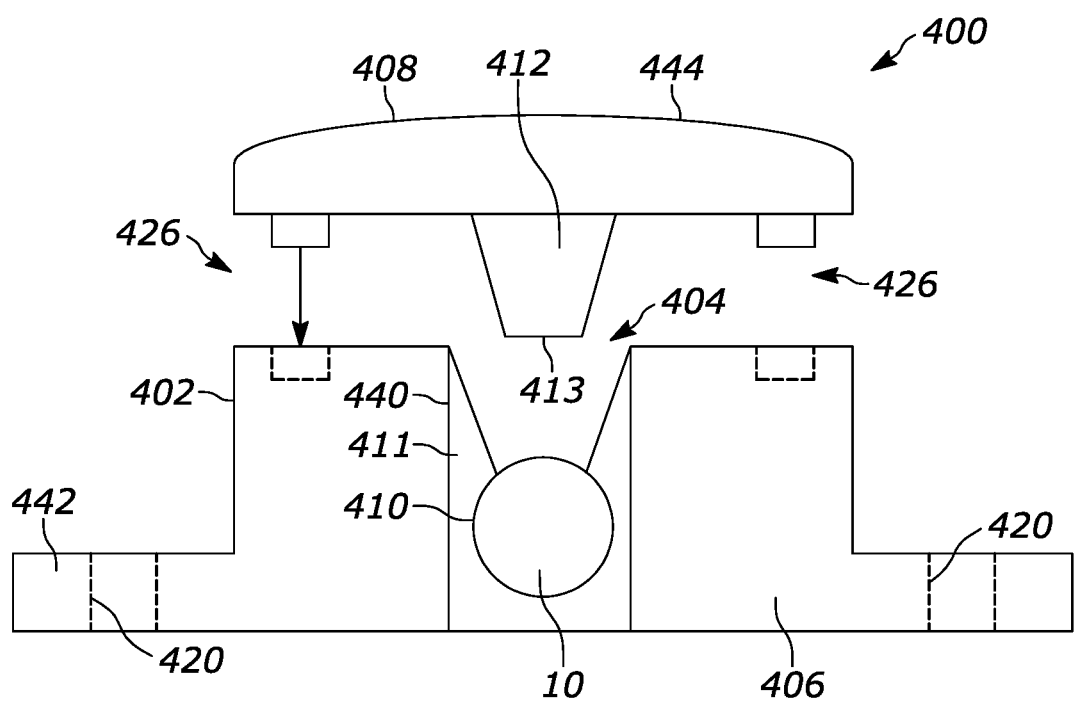
FIG. 21 is a front elevational view of a fifth example fixation device for a catheter showing a catheter loaded into a recess defined by a base of the fixation device with a cover of the fixation device in an open configuration.

Fourth and fifth example fixation devices 400 for a catheter 10 are shown in FIGS. 20 and 21. The fixation devices 400 include a body 402 that defines a bore 404 for reception of the catheter 10. In both forms, the body 402 includes a first body portion or base 406 that defines a bore portion 410 for reception of the catheter 10. The bore portion 410 of this form includes a channel or slot opening 440 extending the longitudinal length of the first body portion 406 and a membrane 411 disposed within the channel 440. As shown, the membrane 411 has an inverted wedge or concave cross-section in a plane transverse to the longitudinal length of the body portion 406, such that the space between the sides of the membrane 411 is reduced to less than an outer diameter of the catheter 10. In one example, the membrane 411 can be made from thermoplastic polyurethane/silicone and the first body portion 406 can be made from PEEK. With this configuration, the catheter 10 can be inserted into the membrane 411 until the membrane 411 clamps onto the catheter 10 to fix the catheter 10 relative to the body 402.

As shown, the first body portion 406 can include outwardly projecting flanges 442 that can have one or more suture openings 420 extending therethrough to secure the fixation device 400 to tissue. For example, the body 402 can include one suture opening 420 on either side of the bore 404 or four suture openings 420 extending through corners of the body 402. By having suture openings 420 on both sides of the bore 404, sutures will securely hold a catheter 10 in a desired location along the tissue of a patient.

In the second form shown in FIG. 21, the body 402 can further include a second body portion or cover 408 that is separate from and engagable with the first body portion 406. The body portions 406, 408 are movable with respect to one another between an open configuration where the catheter 10 can be placed at least partially within the bore 404 and a closed configuration where a length of the catheter 10 is enclosed and retained within the bore 404. If desired, the bore 404 can include radiused ends (not shown) which allow the catheter 10 to flex or travel in directions angled from a longitudinal axis of the body 402. Advantageously, an outer surface 444 of the second body portion 408 can have a curved atraumatic configuration to avoid tissue erosion.

As shown, the second body portion 408 includes a second bore portion 412, where the first and second bore portions 410, 412 cooperate to form the bore 404. The second bore portion 412 is a projection or wall that is sized to fit within the channel 440 of the first bore portion 410. In the illustrated form, the wall 412 is sized to extend at least partially between the sides of the membrane 411 to engage the catheter 10 positioned therebetween. An end surface 413 of the wall 412 can be generally flat as shown, convex, or concave as desired. Moreover, the wall 412 can have a tapered/wedge profile to generally match an angle or curvature of the sides of the membrane 411. The wall 412 can be made from the same material as the membrane 411, such as a thermoplastic polyurethane/silicone, such that the material of the wall 412 and member 422 engage one another and compress around the catheter 10 to secure the catheter 10 within the device 400 when the body portions 406, 408 are in the closed configuration.

The body portions 406, 408 are separate components that can be coupled together with a connector 426 to secure the body portions 406, 408 in the closed configuration to thereby enclose the length of the catheter 10 in the device 400. By one approach, the connector 426 can be a snap-fit connector with male and female components. Alternatively, the connector 426 can be a press fit connection with friction force holding the body portions 406, 408 together.

Figure 22:
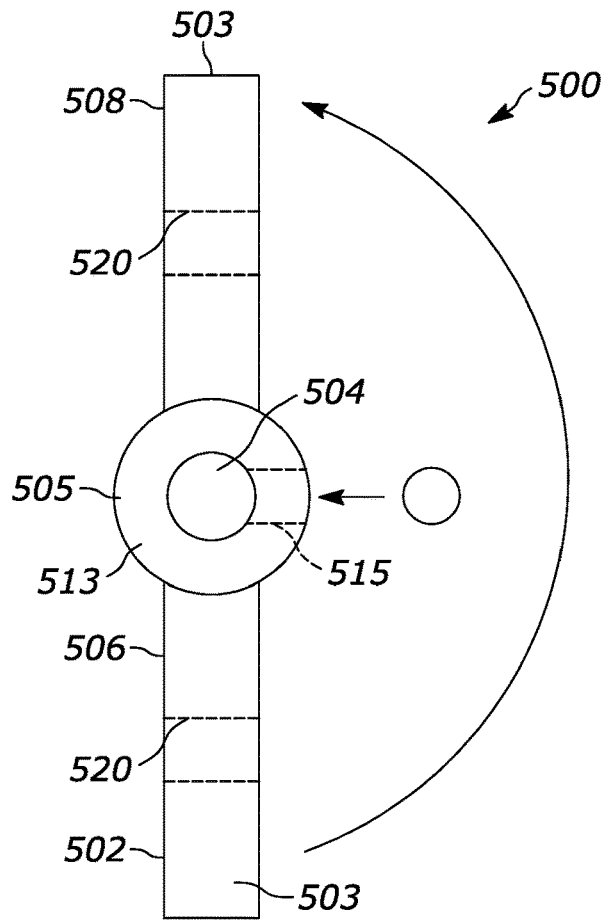
FIG. 22 is a front elevational view of a sixth example fixation device for a catheter showing first and second body portions in an open configuration.
Figure 23:
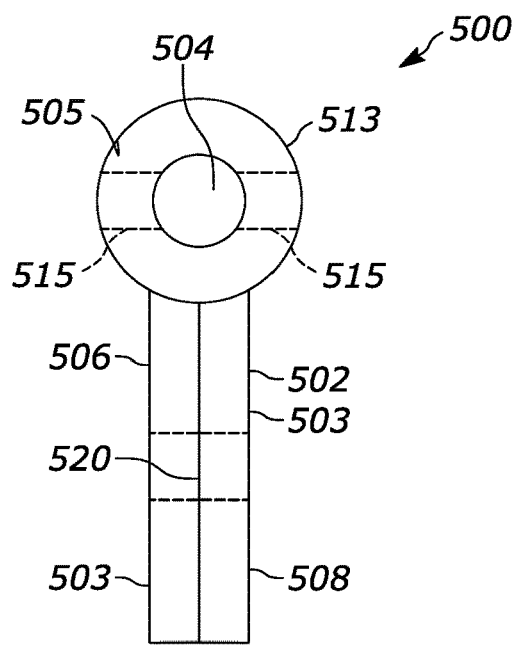
FIG. 23 is a front elevational view of the fixation device of FIG. 22 showing the first and second body portions in a closed configuration.
Figure 24:
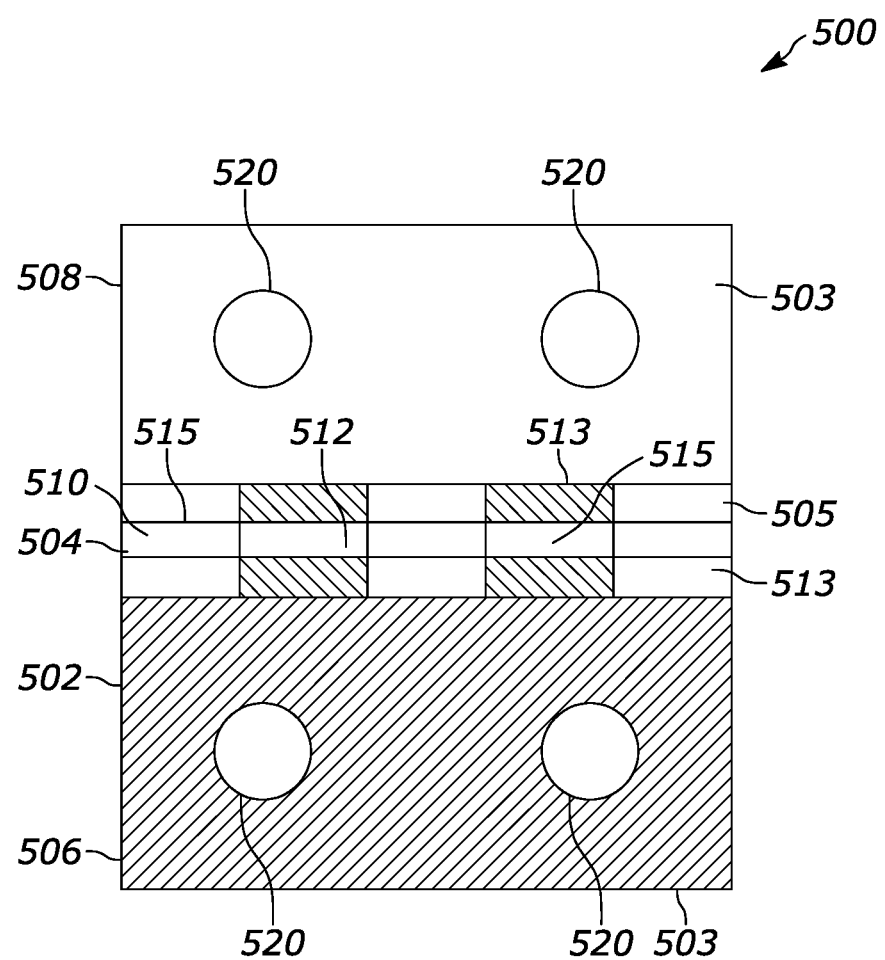
FIG. 24 is a top plan view of the fixation device of FIG. 22 showing the first and second body portions in the open configuration.

A sixth example fixation device 500 for a catheter 10 is shown in FIGS. 22-24. The fixation device 500 includes a body 502 that defines a bore 504 for reception of the catheter 10. In this form, the body 502 includes a first body portion 506 and a second body portion 508 that are pivotably movable with respect to one another from an open configuration where the catheter 10 can be placed at least partially within the bore 504 and a closed configuration where a length of the catheter 10 is enclosed and retained within the bore 504. If desired, the bore 504 can include radiused ends (not shown) which allow the catheter 10 to flex or travel in directions angled from a longitudinal axis of the body 502.

The first body portion 506 includes a first bore portion 510 and the second body portion 508 includes a second bore portion 512, where the first and second bore portions 510, 512 cooperate to form the bore 504. In the illustrated form, the body 502 has a configuration similar to a door hinge assembly with the body portions 506, 508 pivotably coupled together about the bore 504. As shown, the body 502 includes outer plates 503 and a tubular pivot connection 505 between the plates 503 that defines the bore 504. The plates 503 can be generally planar (e.g., between 0-5 degrees, or between 0-10 degrees), such that the plates 503 can extend along one another in a stacked orientation as discussed below. If desired, the plates 503 can have a curved or tapered profile. The body portions 506, 508 can be similar or different materials. Additionally, in some forms, a silicone collar can be disposed within the pivot connection 505 to contact the catheter 10.

Each of the body portions 506, 508 includes one of the plates 503 and the first and second bore portions 510, 512 each provide a portion of the pivot connection 505, where the first and second bore portions 510, 512 interlock and are pivotable with respect to one another to allow the plates 503 to be moved from a spread out configuration in the open position and a stacked configuration in the closed position. For example, each of the bore portions 510, 512 can include longitudinally spaced tubular members 513, where the spaces between the tubular members 513 of the first body portion 506 align with the tubular members 513 of the second body portion 508, and vice versa.

To allow the catheter 10 to be loaded into the bore 504, each of the first and tubular members 513 of the bore portions 510, 512 include a radial slot opening 515 and the body portions 506, 508 can be configured, such that the radial openings 515 of all of the tubular members 513 align with the plates 503 in the open position and are radially offset from one another with the plates in the closed position. If desired, the body portions 506, 508 pivoting with respect to one another to the closed configuration may contain off-axis cam actions to increase a compression load on the catheter 10. For example, one or more of the tubular members 513 may include an off-axis cam member or the tubular members 513 may be configured to rotate off axis to the closed configuration with respect to others of the tubular members 513.

The body 502 can further define one or more suture openings 520 to secure the fixation device 500 to tissue. For example, the body 502 can include two suture openings 520 that extend through both of the plates 503 and are aligned with the plates 503 in the closed position, extending through corners of the body 502. The suture openings 520 can extend through the first body portion 506 and, if aligned with the second body portion 508, through the second body portion 508. The suture openings 520 can be spaced longitudinally from one another along the plates 503 as shown in FIG. 24. Moreover, when the fixation device 500 is sutured in place through the openings 520, the sutures can hold the body portions 506, 508 in the closed configuration, preventing the plates 503 from pivoting and releasing the catheter 10.

Figure 25:
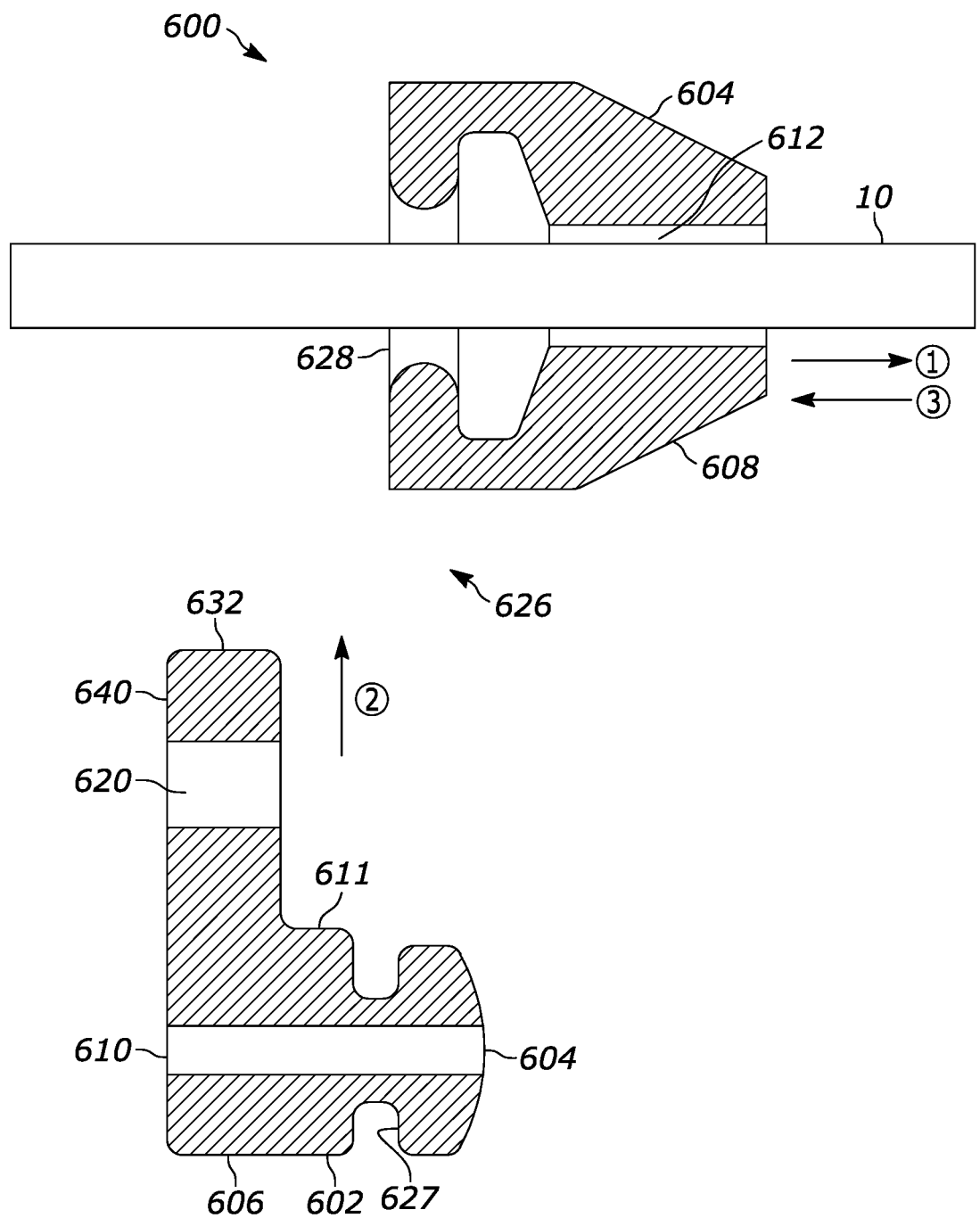
FIG. 25 is a cross-sectional view of a seventh example fixation device for a catheter showing first and second body portions in an open configuration.
Figure 26:
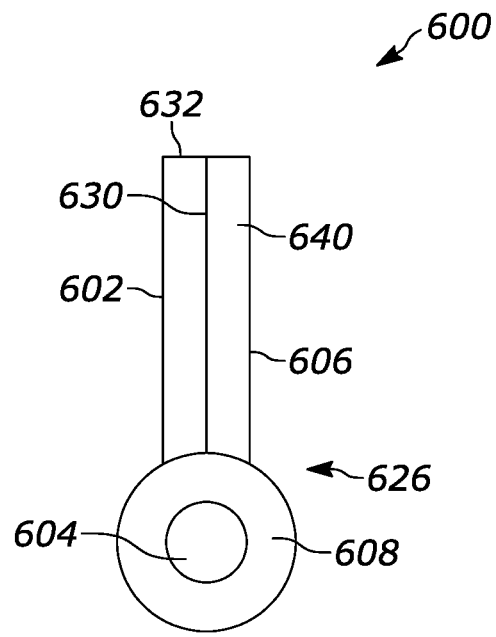
FIG. 26 is a front elevational view of the fixation device of FIG. 25.

A seventh example fixation device 600 for a catheter 10 is shown in FIGS. 25 and 26. The fixation device 600 includes a body 602 that defines a bore 604 for reception of the catheter 10. In this form, the body 602 includes a first body portion 606 and a second body portion 608 that are separate and engagable from an open configuration where the catheter 10 can be placed at least partially within the bore 604 and a closed configuration where a length of the catheter 10 is enclosed and retained within the bore 604. If desired, the bore 604 can include radiused ends (not shown) which allow the catheter 10 to flex or travel in directions angled from a longitudinal axis of the body 602.

As shown, the first body portion 606 includes a first bore portion 610 and the second body portion 608 includes a second bore portion 612, where the first and second bore portions 610, 612 cooperate to form the bore 604. In the illustrated form, the first bore portion 610 is a cylindrical throughbore extending longitudinally through the first body portion 608 and the second bore portion 612 is a cylindrical throughbore extending longitudinally through the second body portion 608, where the throughbores are configured to coaxially align when the body portions 606, 608 are coupled together. The first bore portion 610 can be sized to have enough surface area and the inner diameter thereof can be sized with an interference fit to securely engage and retain a length of the catheter 10 within the device 600. By one approach, the body portions 606, 608 can be made from silicone. Additionally, both silicone components can be made for like durometer materials or different durometers to provide adequate and secure holding capabilities.

As shown, the body portions 606, 608 are separate components that secure together when joined. In the illustrated form, the first body portion 606 includes a tubular projection 611 extending generally along the longitudinal axis, where the first bore portion 610 is defined in the tubular projection 611, and a flange 640 extending transversely away from the tubular projection 611. To mount the first body portion 606 to the catheter 10, the first body portion 606 includes a slit 630 extending along a height thereof transverse to the longitudinal axis from a top edge 632 through the flange 640 and a portion of the tubular projection 611 to the first bore portion 610. So configured, the first body portion 606 can be divided along the slit 630 to provide access to the first bore portion 610 and the catheter 10 can be placed therein.

The second body portion 608 is an annular member configured to couple to the tubular projection 611 to thereby hold the first body portion 608 together and thereby hold the body portions 606, 608 in the closed configuration. With this configuration, the annular member 608 is loaded onto the catheter 10 first and then the first body portion 606 is side loaded onto the catheter 10 at a desired location along the catheter 10 through the slit 630. Thereafter, the body portions 606, 608 can be coupled together to secure the body 602 in the closed configuration.

By one approach, the annular member 608 and tubular projection 611 can be sized to press-fit together, such that friction holds the body 602 in the closed configuration. In another form, the body portions 606, 608 can include a snap-fit connector 626 to secure the body portions 606, 608 in the closed configuration to thereby enclose the length of the catheter 10 in the device 600. For example, the tubular projection 611 can include an annular groove 627 extending therearound adjacent to an end thereof and the annular member 608 can include a radially inwardly extending lip 628 sized and configured to seat within the groove 627 when the annular member 608 is slip fit onto the tubular projection 611. Moreover, the annular member 608 can have a tapered configuration to minimize tissue erosion.

If desired, the body 602 can further define one or more suture openings 620 to secure the fixation device 600 to tissue. For example, the first body portion 606 can include one or more suture openings 620 extending through the split flange 640 to securely hold a catheter 10 in a desired location along the tissue of a patient. Moreover, when the fixation device 600 is sutured in place through the openings 620, the sutures can aid in holding the first body portion closed, preventing the first body portion 606 from dividing along the slit 630 and releasing the catheter 10.

In some forms, the body 602 can be made from or have the inner surface of the bore portions 606, 608 coated or layered with a similar or identical material to the catheter 10. This configuration can increase the coefficient of friction between the device 600 and the catheter 10, which determines the retention force of the catheter.

Figure 27:
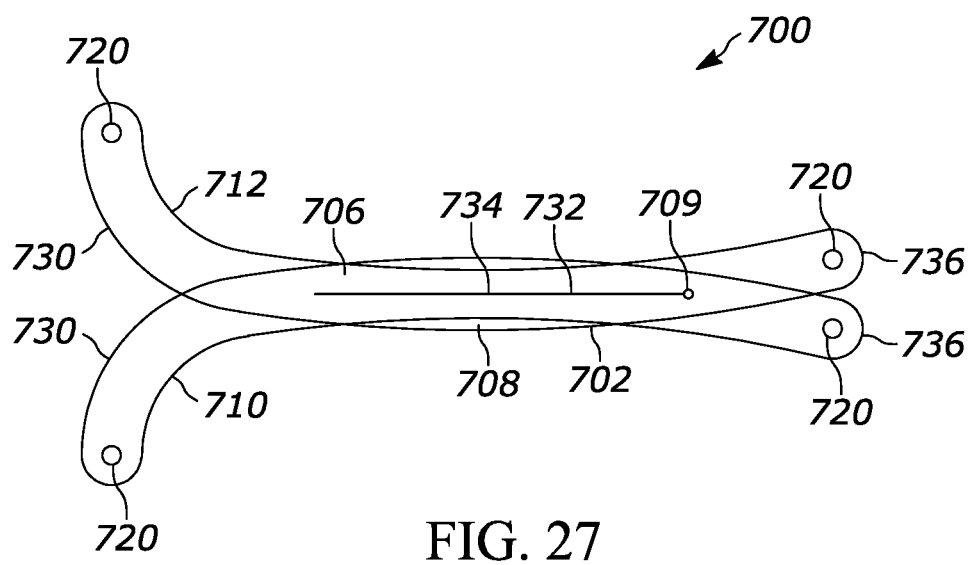
FIG. 27 is a front elevational view of an eighth example fixation device for a catheter showing first and second body portions in a closed configuration.
Figure 28:
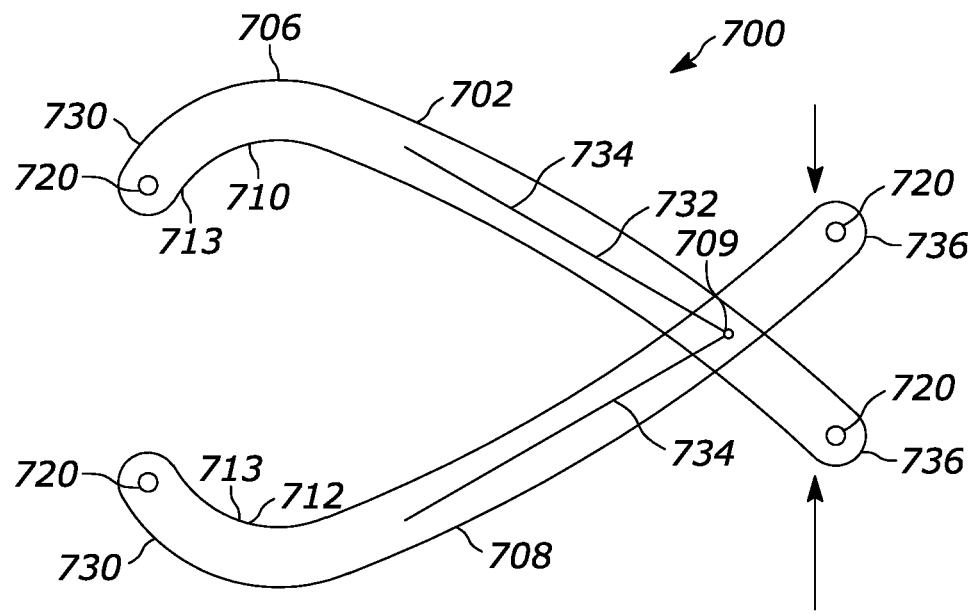
FIG. 28 is a front elevational view of the fixation device of FIG. 27 showing the first and second body portions in an open configuration.
Figure 29:
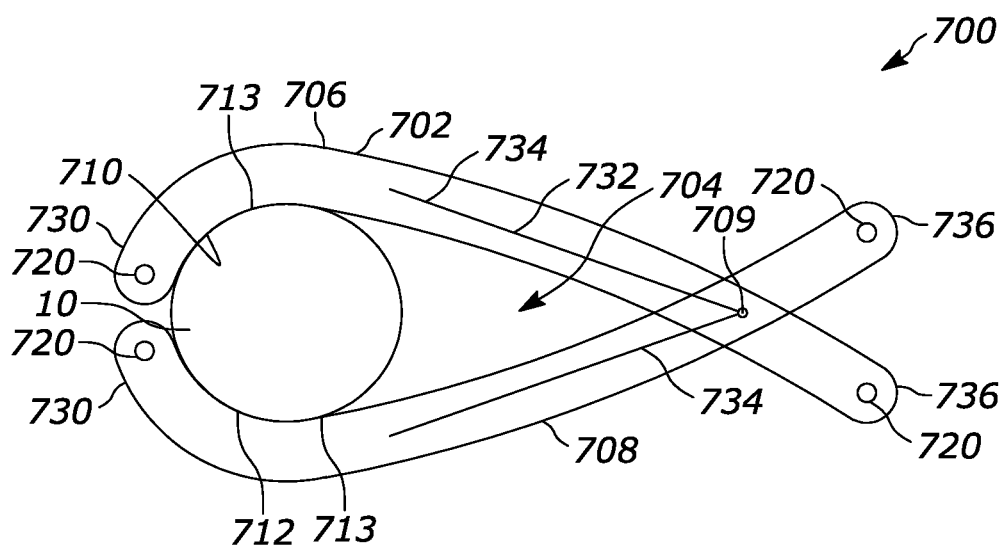
FIG. 29 is a front elevational view of the fixation device of FIG. 27 showing the first and second body portions in a closed configuration with a catheter retained therein.

An eighth example fixation device 700 for a catheter 10 is shown in FIGS. 27-29. The fixation device 700 includes a body 702 that defines a bore 704 for reception of the catheter 10. In this form, the body 702 includes separate first and second body portions 706, 708 that are pivotably coupled together about a pivot 709. The body portions 706, 708 are pivotable with respect to one another from an open configuration where the catheter 10 can be placed at least partially within the bore 704 and a closed configuration where a length of the catheter 10 is enclosed and retained within the bore 704. If desired, the bore 704 can include radiused ends (not shown) which allow the catheter 10 to flex or travel in directions angled from a longitudinal axis of the body 702.

The first body portion 706 includes a first bore portion 710 and the second body portion 708 includes a second bore portion 712, where the first and second bore portions 710, 712 cooperate to form the bore 704. In the illustrated form, the body 702 has a clamp configuration with distal ends 730 of the body portions 706, 708 biased towards one another by a biasing member or assembly 732. The distal ends 730 each include an inwardly oriented concave surface 713 forming the bore portions 710, 712. In the illustrated form, the distal ends 730 have a curved configuration providing the concave surfaces 713. For example, the biasing member 732 can be a torsion spring with arms 734 extending along each of the body portions 706, 708. The body portions 706, 708 can be similar or different materials. Additionally, in some forms, the concave surfaces 713 can be silicone or layered with silicone to contact the catheter 10.

As shown, proximal ends 736 of the body portions 706, 708 are disposed on an opposite side of the pivot 709 from the distal ends 730, such that the proximal ends 736 are biased away from one another by the biasing member 732. So configured, to load the catheter 10 into the bore 704, a user can squeeze the proximal ends 736 of the body portions 706, 708 together to pivot the distal ends 730 away from one another to position the body portions 706, 708 in the open configuration. The catheter 10 can then be positioned between the concave surfaces 713 and the user can release the proximal ends 736, allowing the biasing member 732 to move the distal ends 730 together to capture the catheter 10 in the bore 704 with the body portions 706, 708 in the closed configuration.

The body 702 can further define one or more suture openings 720 to secure the fixation device 700 to tissue. For example, the body portions 706, 708 can include suture openings 720 that extend through the distal and/or proximal ends 730, 736 thereof. Moreover, when the fixation device 700 is sutured in place through the openings 720, the sutures can hold the body portions 706, 708 in the closed configuration, preventing the body portions 706, 708 from pivoting and releasing the catheter 10.

Figure 30:
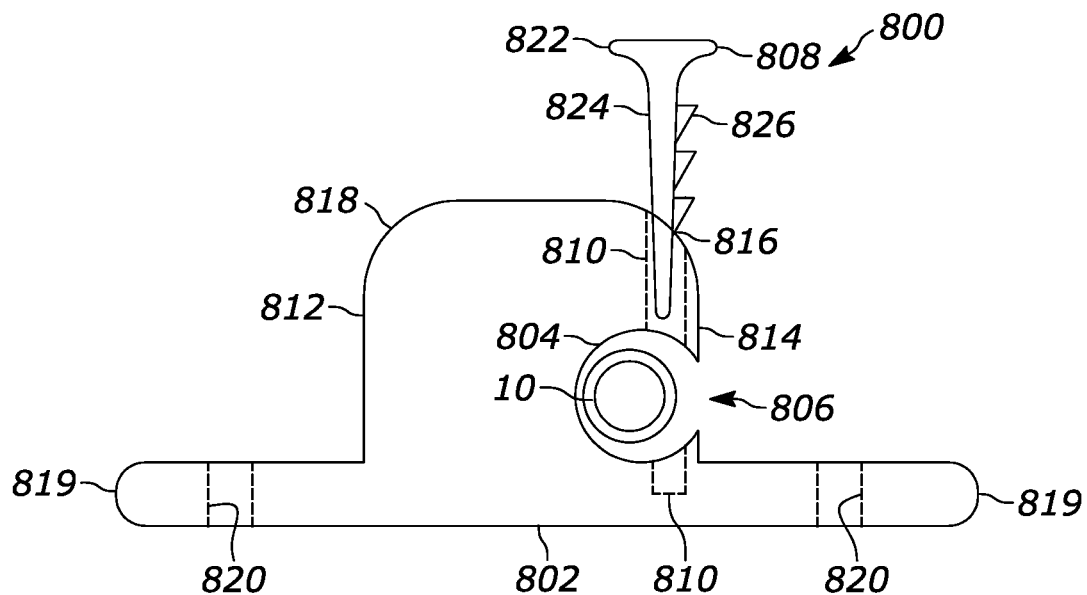
FIG. 30 is a front elevational view of a ninth example fixation device for a catheter showing a body having a catheter inserted into a bore defined therein and a securing member in an unsecured configuration.
Figure 31:
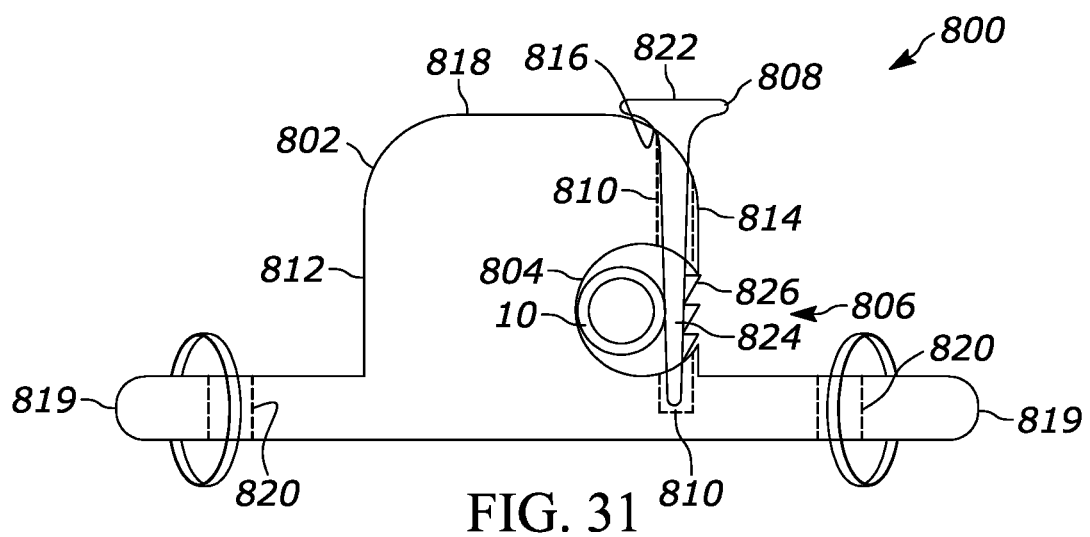
FIG. 31 is a front elevational view of the fixation device of FIG. 30 showing the securing member in a secured configuration.
Figure 32:
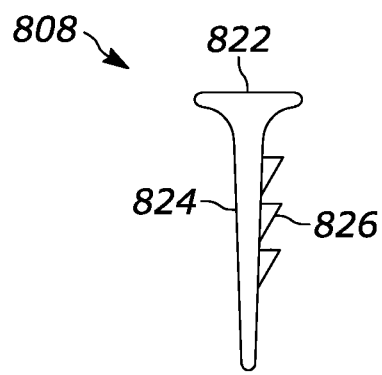
FIG. 32 is a front elevational view of another example securing member for the fixation device of FIG. 30.

A ninth example fixation device 800 is shown in FIGS. 30-32. The fixation device 800 includes a body 802 defining a bore 804 having an opening 806 extending along a longitudinal length thereof. With this configuration, the catheter 10 can be side-loaded into the bore 804 through the opening 806. As shown, the fixation device 800 further includes a securing member 808 that is configured to couple to the body 802 and extend across the opening 806 of the bore 804 after the catheter 10 has been positioned therein to enclose a length of the catheter 10 in the bore 804. In the illustrated form, the body 802 defines a cavity 810 having portions aligned transversely across the bore 804 offset from a central longitudinal axis thereof.

As shown, the bore 804 can have a diameter larger than an outer diameter of the catheter 10, such that the catheter 10 can be shifted radially in the bore 804. Advantageously, the cavity 810 can be aligned across the bore 804, so that a distance between the securing member 808 inserted into the cavity 810 and a surface of the bore 804 across the longitudinal axis thereof can be smaller than the outer diameter of the catheter 10. So configured, when the securing member 808 is inserted into the cavity 810, both the securing member 808 and the bore 804 engages the catheter 10 with a predetermined compressive force to retain a length of the catheter 10 in the fixation device 800 and prevent migration of the catheter 10 through the device 800.

In the illustrated form, the bore 804 extends through a raised central portion 812 of the body 802 with the opening 806 defined in a side 814 of the central portion 812. Further, with this configuration, the cavity 810 can be generally vertical and transverse to the longitudinal axis of the bore with an access opening 816 defined in a top 818 of the central portion 812. Of course, other configurations can alternatively be utilized.

The body 802 can also include flanges 819 that extend outwardly from one or both sides of the raised central portion 812. Further, one or more suture openings 820 can extend through the flanges 819 to secure the fixation device 800 to tissue. For example, the body 802 can include one suture opening 820 on either side of the bore 804 or four suture openings 820 extending through corners of the body 802. When the fixation device 800 is sutured in place through the openings 820, the sutures can hold the body 802 in place to securely hold a catheter 10 in a desired location along the tissue of a patient.

In this form, the securing member 808 can be a pin with a head 822 and an elongate shaft 824 extending from the head 822. The shaft 824 is sized to be disposed within the cavity 810 to retain the catheter 10 within the bore 804, as discussed above. Advantageously, the cavity 810 and pin 808 can be sized so that when the catheter is loaded into the fixation device 800 at a desired location, a user can push the pin 808 into the cavity 810 until the head 822 is flush with body 802, such as the top 818 thereof as shown. In some examples, the body 802 and pin 808 can be made from a relatively hard material, such as PEEK or a metal.

If desired, the pin 808 can include retention structure 826 to secure the pin 808 to the body 802 and resist removal or migration of the pin from the cavity 810. For example, the pin 808 can include one or more barbs 826 that extend radially outwardly from the shaft 824 to engage the body 802 as the shaft 824 is inserted into the cavity 810. Of course, the opposite configuration could also be utilized with the body 802 having barbs extending into the cavity 810 to engage recesses in the shaft 824. In the illustrated form, the pin 808 includes several barbs 826 spaced along a height of the shaft 824 to engage the body on one or both sides of the opening 806 to the bore 804. As shown, the pin 808 can be oriented during insertion into the cavity 810 so that the barbs 826 extend away from the catheter 10. The barbs 826 can further be angled to resist removal of the shaft 824 from the body 802 to ensure that the catheter 10 is retained after the fixation device 800 is secured in place. Advantageously, with this configuration, the fixation device 800 can be provided with the pin 808 partially preassembled into the cavity 810 with the opening 806 to the bore 804 unblocked. When the fixation device 800 is positioned at a desired location along the catheter 800, a user can simply press down on the pin 808 until the head 822 is flush with the body 802 so that the pin 808 closes off the opening 806 to the bore 804 and engages the catheter 10, as discussed above.

In a further form, the shaft 824 can have a tapering profile as shown in FIG. 32, such that the shaft 824 is relatively wider adjacent to the head 822 and relatively narrower at the distal end. So configured, the further down the cavity 810 that the pin 808 is advanced, the greater amount that the catheter 10 is compressed.

Tenth and eleventh example fixation devices 900 are shown in FIGS. 33-38. The fixation device 900 includes a body 902 defining a bore 904 having a longitudinal opening 906 extending along a length thereof. With this configuration, the catheter 10 can be top-loaded into the bore 904 through the opening 906. As shown, the fixation device 900 further includes a securing member 908 that is configured to couple to the body 902 and extend across the opening 906 of the bore 904 after the catheter 10 has been positioned therein to enclose a length of the catheter 10 in the bore 904.

Figure 33:
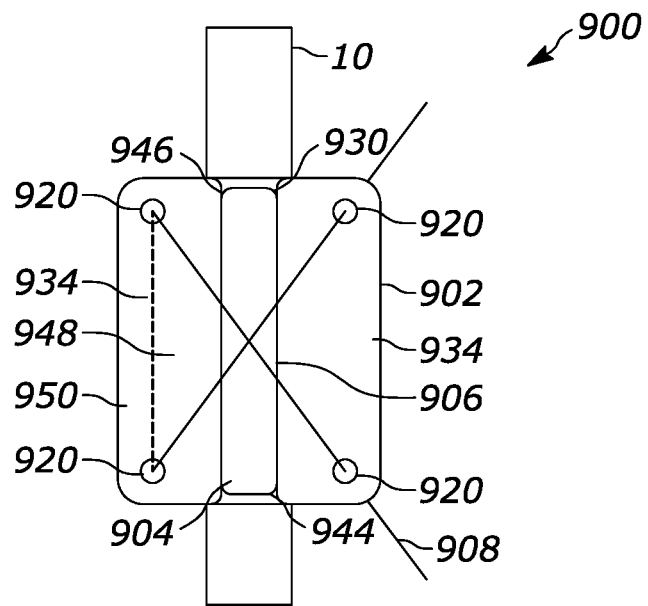
FIG. 33 is a top plan view of a tenth example fixation device for a catheter showing a body having a catheter inserted into a bore defined therein and a securing member in a secured configuration.
Figure 34:
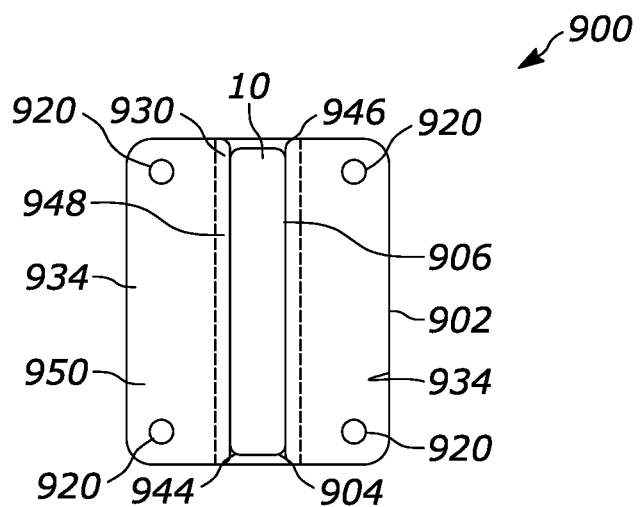
FIG. 34 is a top plan view of the fixation device of FIG. 33 without the securing member.
Figure 36:
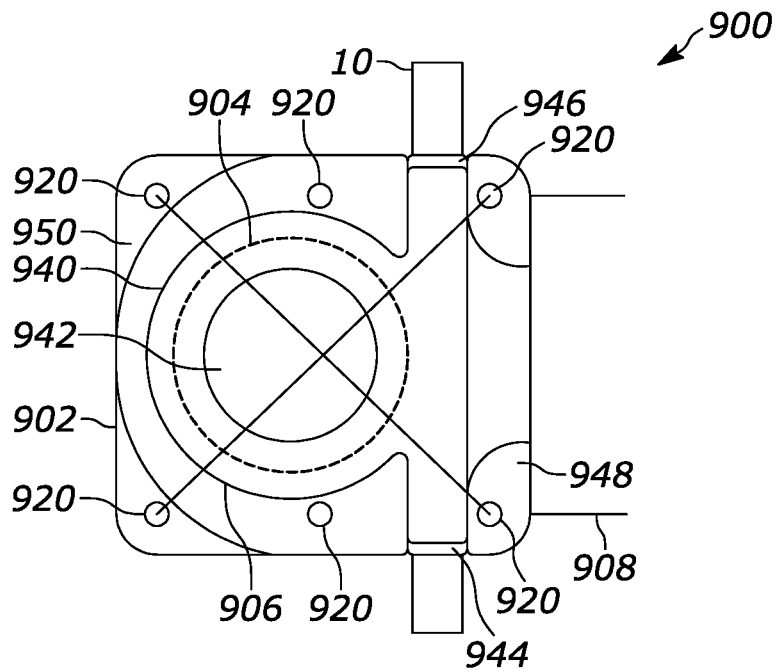
FIG. 36 is a top plan view of an eleventh example fixation device for a catheter showing a body having a catheter inserted into a bore defined therein and a securing member in a secured configuration.

As shown, the body 902 can include an array of suture openings 920 extending therethrough to secure the fixation device 900 to tissue. For example, the body 902 can include one suture opening 920 on either side of the bore 904, four suture openings 920 extending through corners of the body 902 as shown in FIGS. 33 and 34, six suture openings 920 as shown in FIG. 36, or other combinations. Advantageously, in these forms, the securing member 908 can be sutures that extend across the body 902 and the opening 906 to the bore 904 to thereby enclose a length of the catheter 10 in the bore 904. Further, the sutures 908 can function as normal sutures and hold the body 902 in place to securely hold the catheter 10 in a desired location along the tissue of a patient.

Figure 35:
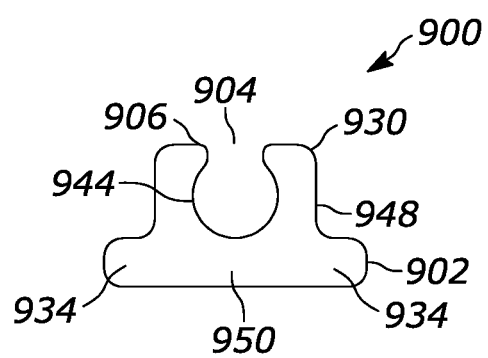
FIG. 35 is a front elevational view of the fixation device of FIG. 33 without the securing member.

In the first form shown in FIGS. 33-35, the bore 904 can be generally linear with a top portion 930 formed by upstanding walls 932 that define the opening 906 therebetween. The opening 906 can have a width less than an outer diameter of the catheter 10, such that the walls 932 can be deformed to be resiliently flexed away from one another to insert the catheter 10 into the bore 904 and can be configured to at least partially return to an unflexed position to trap the catheter 10 within the bore 904. The walls 932 can have a curved configuration as shown that is generally complementary to an edge of the bore 904. Further, the body 902 can include flanges 934 that extend outwardly from one or both sides of the walls 932. With this configuration, the sutures 908 can be threaded through the suture openings 920 extending through corners of the flanges 934 to extend over the opening 906 to the bore 904. When pulled tight, the sutures 908 compress on the walls 932 to thereby tightly engage the catheter 10 with the body 902. The sutures 908 can be disposed in an X-configuration as shown, or can extend transversely across the body 902.

Figure 37:
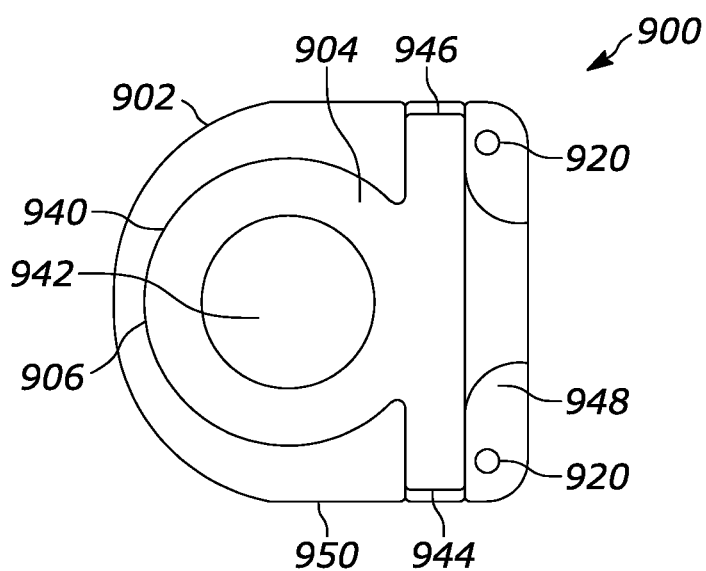
FIG. 37 is a top plan view of the fixation device of FIG. 36 without the securing member.
Figure 38:
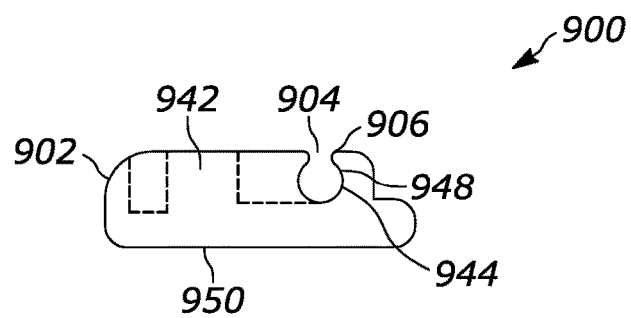
FIG. 38 is a front elevational view of the fixation device of FIG. 36 without the securing member.

In the second form shown in FIGS. 36-38, the bore 904 includes an annular portion 940 defining a circular path for the bore 904 around a central peg 942 of the body 902. To insert the catheter 10 into the bore 904, the catheter 10 is placed at an inlet 944 of the bore 904, wrapped around the peg 942 until it overlaps itself, and then placed at an outlet 946 of the bore 904.

The bore 904 can be sized with an inner diameter greater than an outer diameter of the catheter 10, such that the catheter 10 is initially loosely disposed within the bore 904. Thereafter, a user can pull on catheter 10 adjacent to the inlet 944 and/or outlet 946 to tighten the catheter 10 around the peg 942. With this configuration, the peg 942 can at least partially provide a portion of the securing member 908. By one approach, at least a portion of the bore 904, such as adjacent to the inlet 944 and outlet 946 thereof, can be formed by upstanding walls 948 that project away from a base 950 of the body 902 and at least partially define the opening 906. The opening 906 can have a width less than an outer diameter of the catheter 10, such that the walls 948 can be deformed to be resiliently flexed to insert the catheter 10 into the bore 904 and can be configured to at least partially return to an unflexed position to trap the catheter 10 within the bore 904. The walls 948 can have a curved configuration as shown that is generally complementary to the cylindrical outer surface of the catheter 10.

Figure 39:
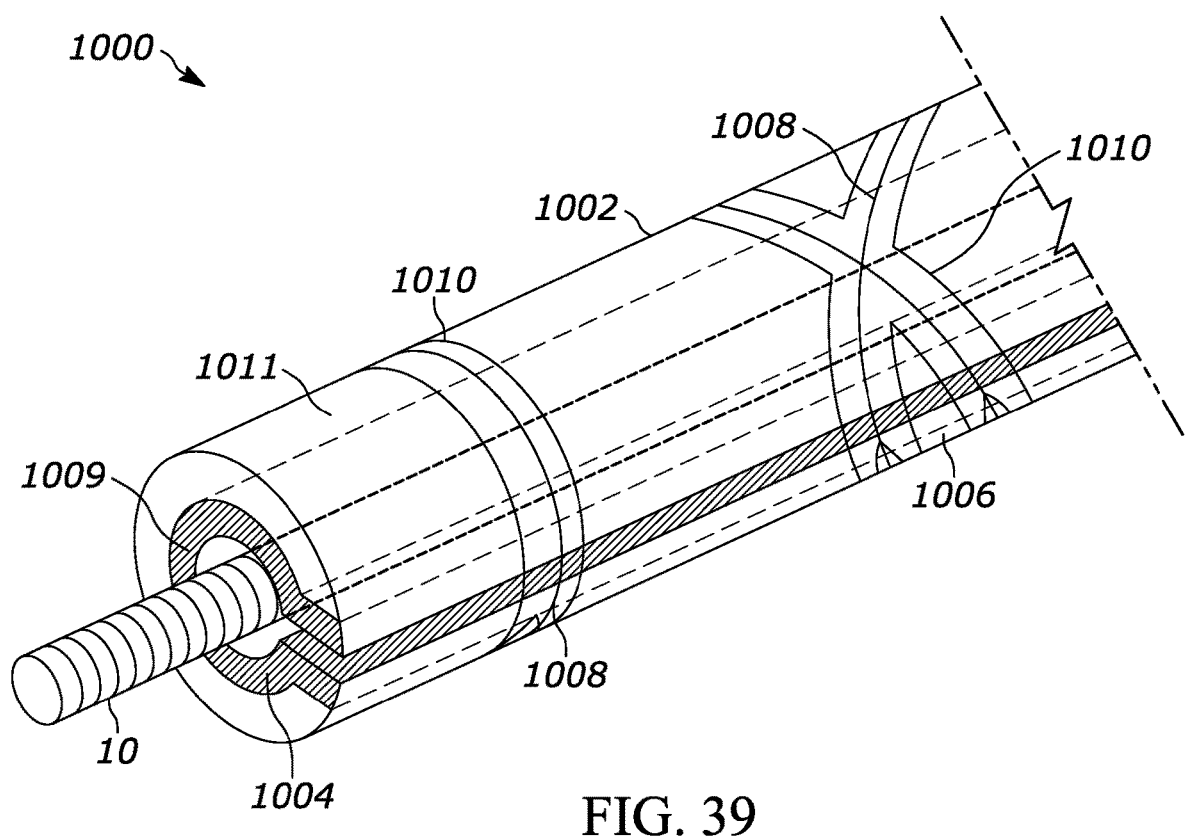
FIG. 39 is a sectional perspective view of a twelfth example fixation device for a catheter.
Figure 40:
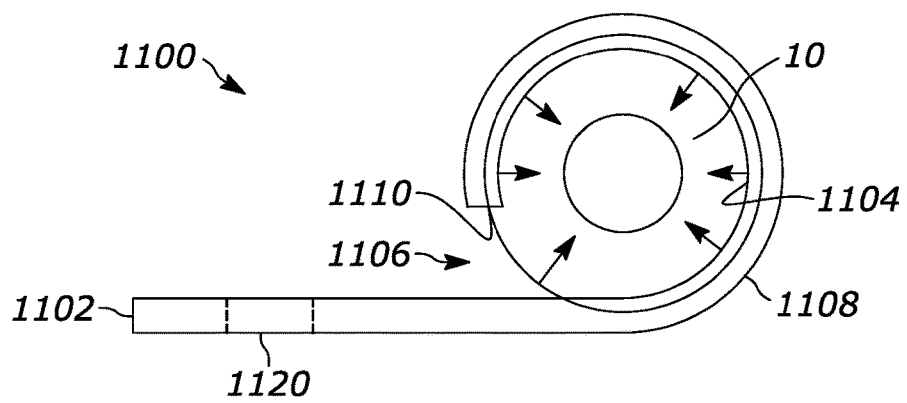
FIG. 40 is a front elevational view of a thirteenth example fixation device for a catheter.

A twelfth example fixation device 1000 is shown in FIG. 39. The fixation device 1000 includes a body 1002 having a tubular configuration defining a bore 1004 having an opening or slit 1006 extending along a longitudinal length thereof. With this configuration, the catheter 10 can be side-loaded into the bore 1004 through the opening 1006. As shown, the fixation device 1000 further includes a securing member 1008 that is configured to couple to the body 1002 and extend across the opening 1006 of the bore 1004 after the catheter 10 has been positioned therein to enclose a length of the catheter 10 in the bore 1004. In this form, the securing member 1008 member is a suture that is wrapped in a spiral configuration around a longitudinal length of the body 1002. With this configuration, the suture 1008 can secure the device 1000 to tissue and retain the catheter 10 within the bore 1004.

As shown, the bore 1004 can have a diameter larger than an outer diameter of the catheter 10, such that the catheter 10 can initially be shifted radially in the bore 1004. Advantageously, in this form, the suture 1008 can be tightened around the body 1002 to compress the body 1002 around the outer diameter of the catheter 10 to retain the length of the catheter 10 within the body 1002 with a predetermined compressive force and prevent migration of the catheter 10 through the device 1000. The force to which the suture 1008 is wrapped around the body 1002 and then tied to the surrounding fascia or other tissue can be utilized to drive to the retention force of the catheter 10. In some embodiments, the device 1000 can further include a material or layer 1009 disposed within the body 1002 and extending around the bore 1004. The layer 1009 can be composed of a hard material, e.g., PEEK, for contacting the catheter 10 and maintaining the curvature of the body 1002 with the outer portions of the body 1002 being a soft material, e.g., silicone, for contacting tissue. In some examples, the body 1002 can be made from a thermoplastic material.

In the illustrated form, the body 1002 can further define one or more spiral grooves 1010 in an outer surface 1011 thereof extending along a longitudinal length of the body 1002. For example, the grooves 1010 can intersect one another as they spiral around the body 1002, such that sutures 1008 received within the grooves 1010 can overlap one another and extend across the opening 1006 to the bore 1004.

Figure 41:
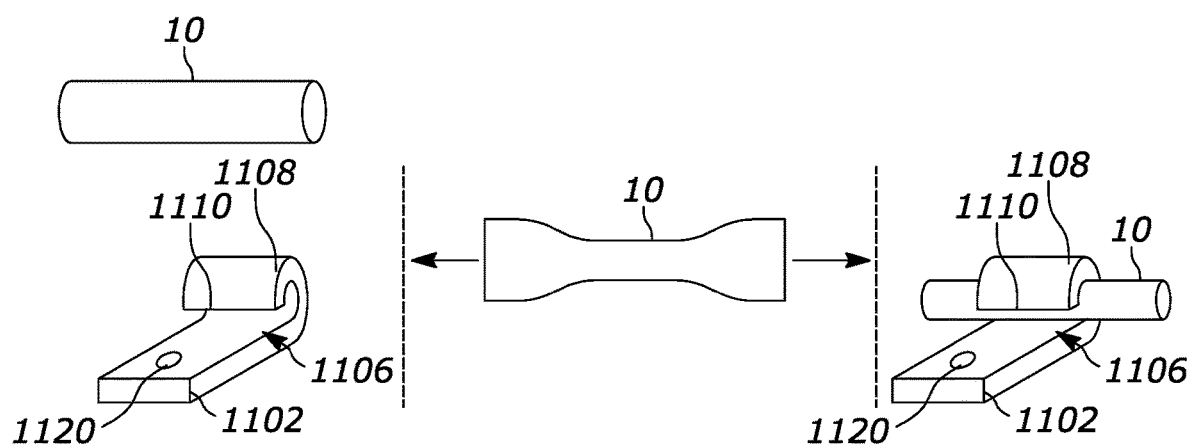
FIG. 41 is a perspective view of the fixation device of FIG. 40 showing a loading process for a catheter.
Figure 42:
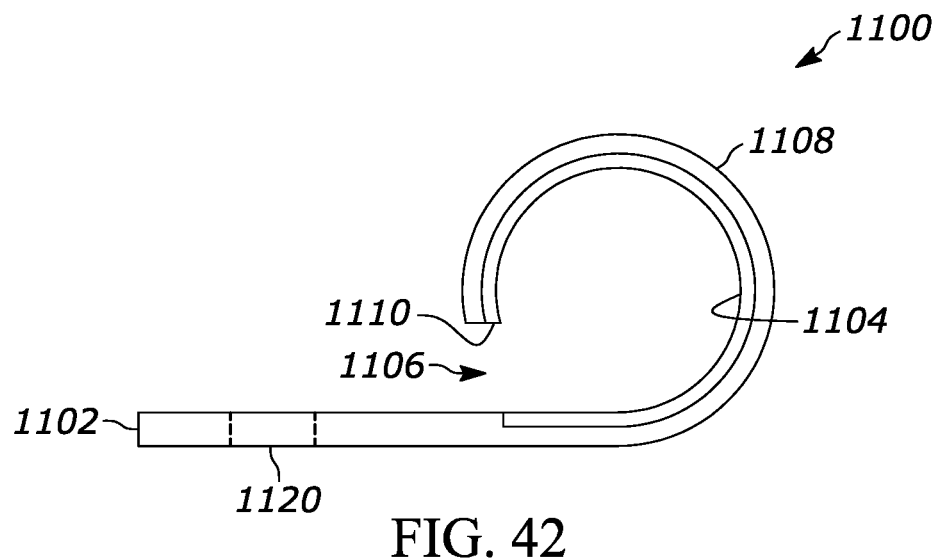
FIG. 42 is a cross-sectional view of the fixation device of FIG. 40 showing a first example configuration.
Figure 43:
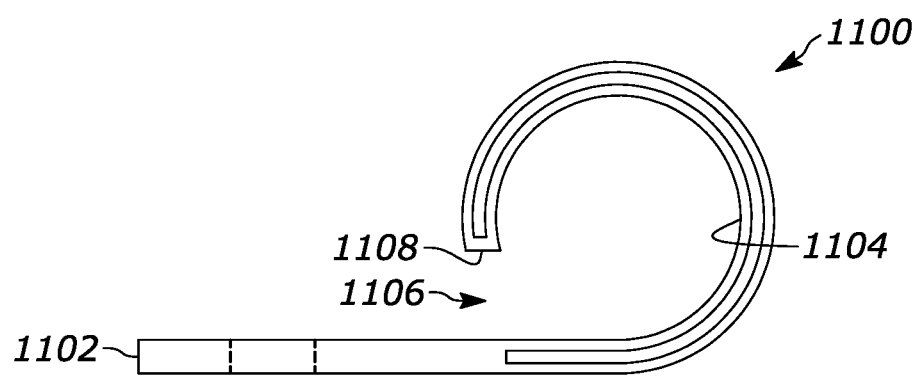
FIG. 43 is a cross-sectional view of the fixation device of FIG. 40 showing a second example configuration.
Figure 44:
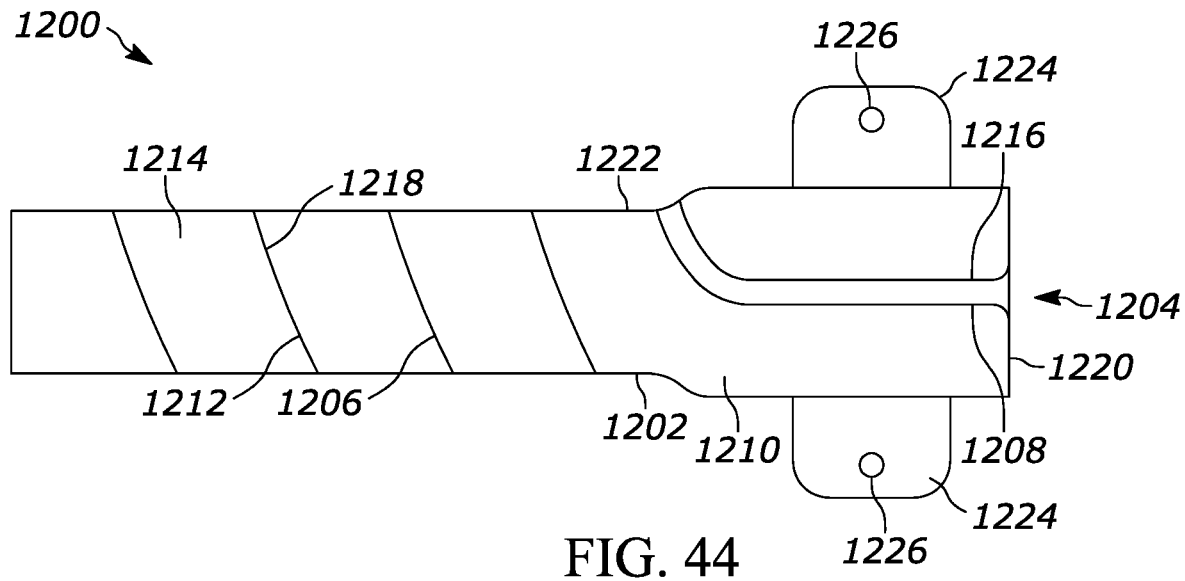
FIG. 44 is a top plan view of a fourteenth example fixation device for a catheter.
Figure 45:
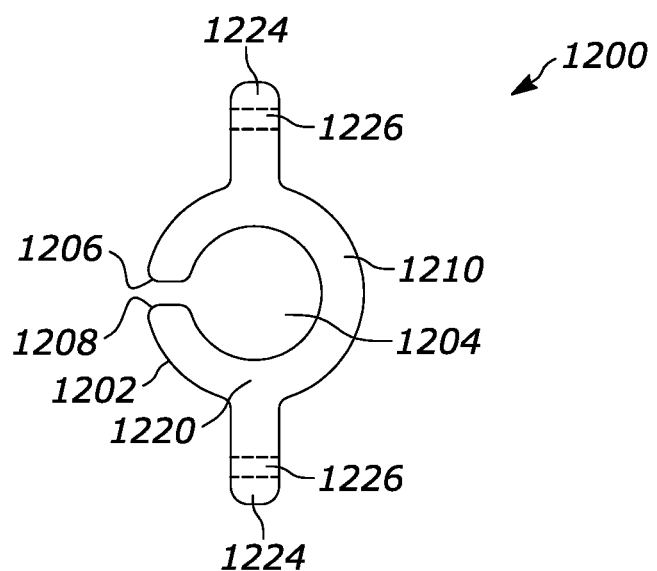
FIG. 45 is a front elevational view of the fixation device of FIG. 44.
Figure 46:
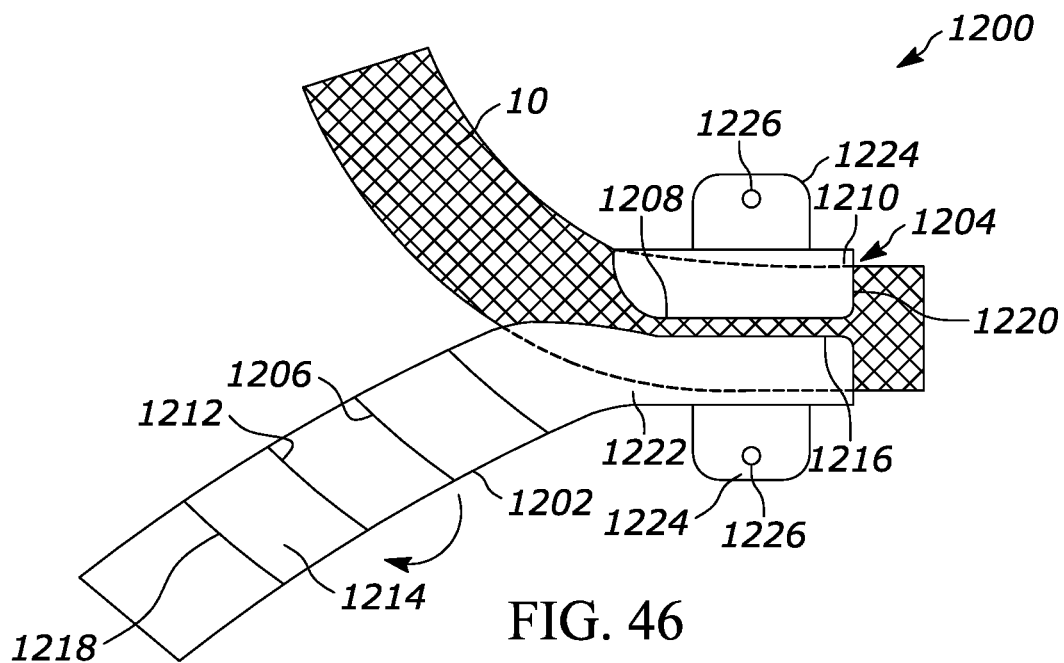
FIG. 46 is a top plan view of the fixation device of FIG. 44 showing a catheter in a partially loaded state.
Figure 47:
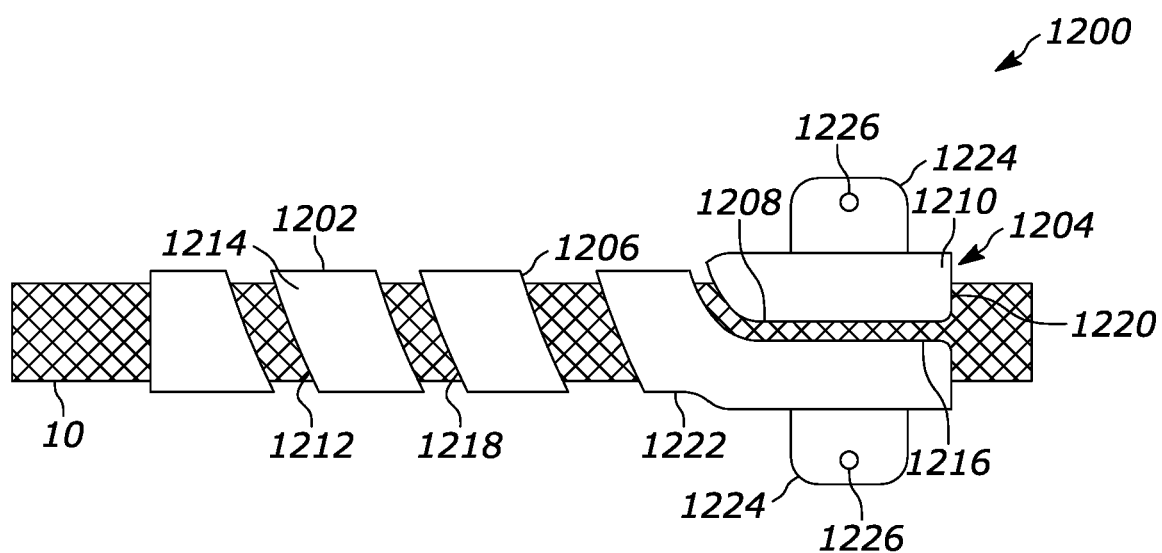
FIG. 47 is a top plan view of the fixation device of FIG. 44 showing a catheter in a fully loaded state.

A thirteenth example fixation device 1100 is shown in FIGS. 40-43. The fixation device 1100 includes a body 1102 defining a bore 1104 having an opening or slit 1106 extending along a longitudinal length thereof. With this configuration, the catheter 10 can be side-loaded into the bore 1104 through the opening 1106. As shown, the body 1102 can include a distal end 1108 having a curved configuration to define the bore 1104. An edge 1110 of the distal end 1108 is curved back to an intermediate portion of the body 1102 and spaced therefrom to define the longitudinal opening 1106 to the bore 1104. The opening 1106 can be sized to have a width smaller than an outer diameter of the catheter 10. With this configuration, as shown in FIG. 41, the catheter 10 can be resiliently deformed by stretching the catheter 10 axially to reduce the outer diameter thereof, such that the stretched catheter 10 can fit through the longitudinal opening 1106 to dispose the catheter 10 within the bore 1104. Moreover, the inner diameter of the bore 1104 can be smaller than the outer diameter of the catheter 10, such that when the catheter 10 is deformed and loaded into the bore 1104 through the opening 1106, the catheter 10 will relax and resiliently return toward its original outer diameter, but the distal end 1108 of the body 1102 defining the bore 1104 will eventually restrict further radial expansion and apply a compressive force on the catheter 10, retaining the catheter 10 within the device 1100. The inner diameter of the bore 1104 and outer diameter of the catheter 10 can be configured to provide a sufficient friction and compression force to retain the catheter 10 within the device 1100 without constricting the inner diameter of the catheter 10 to the point where a desired flow rate is impacted.

The body 1102 can have a several different suitable configurations. In one example, the body 1102 can be made from a homogenous material, e.g., silicone. In another example, the body 1102 can include a hard material, e.g., PEEK, extending along an interior surface of the body distal end 1108 for contacting the catheter 10 and maintaining the curvature of the body distal end 1108 with the remaining portions of the body 1102 being a soft material, e.g., silicone, for contacting tissue. In another example, a hard material can be disposed or embedded within the body distal end 1108 to maintain the curvature thereof with the remaining portions of the body 1102 being a soft material.

If desired, the body 1102 can further define one or more suture openings 1120, such as one extending through the body 1102 opposite the distal end 1108 as shown, to secure the fixation device 1100 to tissue.

A fourteenth example fixation device 1200 is shown in FIGS. 44-47. The fixation device 1200 includes a body 1202 having a tubular configuration defining a bore 1204 having an opening or slit 1206 extending along a longitudinal length thereof to load the catheter 10 into the body 1202. In the illustrated form, the opening 1206 includes a loading portion 1208 in a proximal end 1210 of the body 1202 and a spiral portion 1212 in a distal end 1214 of the body 1202. As shown, edges 1216 of the loading portion 1208 are spaced apart from one another in a resting state a distance less than an outer diameter of the catheter 10, while edges 1218 of the spiral portion 1212 can be abutting or closely spaced. Of course, in other embodiments, the edges 1216 of the loading portion can be abutting or closely spaced together similar to the spiral portion 1212.

The loading portion 1208 of the opening 1206 extends longitudinally from an end edge 1220 of the body 1202 along a length of the body proximal end 1210 and then angles outwardly to open through a side of the body proximal end 1210 or through a transition portion 1222 of the body 1202. So configured, the catheter 10 can easily be loaded into the body proximal end 1210 through the loading portion 1208 by deforming the body proximal end 1210 to spread the edges 1216 of the loading portion 1208, such that the catheter 10 extends longitudinally through the body proximal end 1210 and out through the side of the body 1202, such as the proximal end 1210 or the transition portion 1218 thereof. Thereafter, a user can spin the body distal end 1214 around the catheter 10, which causes the catheter 10 to load into the bore 1204 through the spiral portion 1212 of the opening 1206. This action is repeated until the catheter 10 is fully loaded into the bore 1204 within the tubular body 1202.

As shown, the body distal end 1214 can have a reduced inner diameter relative to the body proximal end 1210 with the reduced inner diameter being less than the outer diameter of the catheter 10. The inner diameter of the body proximal end 1210 can be greater than, equal to, or less than the outer diameter of the catheter 10, as desired. Due to the relative sizes of the inner diameter of the body distal end 1214 and the outer diameter of the catheter 10, when the catheter 10 is loaded into the body distal end 1214, the distal end 1214 applies a compressive, retention force to the catheter 10 to retain the catheter 10 within the device 1200. Due to the reduced diameter, loading the catheter 10 into the body distal end 1214 can cause the distal end 1214 to axially stretch with the spiral portion 1212 having a spaced configuration.

The device 1200 can further include one or more tabs 1224 that extend radially outwardly from the body 1202. For example, the tabs 1224 can extend outwardly on opposite sides of the body proximal end 1210 as shown, outwardly from one or both sides of the body distal end 1214, or combinations thereof. Each of the tabs 1224 can further define one or more suture openings 1226 to secure the fixation device 1200 to tissue. By having suture openings 1226 on both sides of the body 1202, sutures will securely hold a catheter 10 in a desired location along the tissue of a patient.

Figure 48:
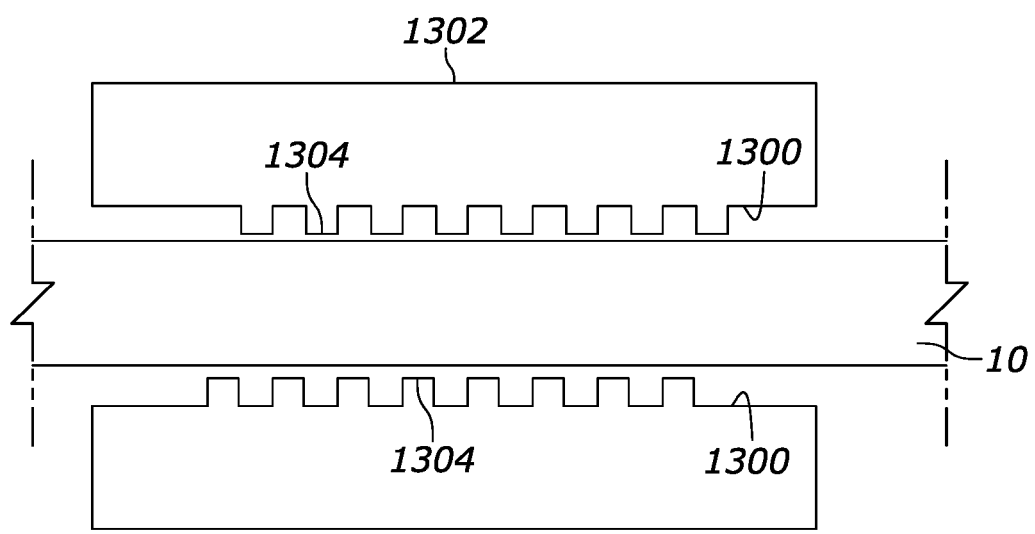
FIG. 48 is a cross-sectional view of a fifteenth example fixation device for a catheter.

For any of the above example fixation devices, surfaces 1300 of the body 1302 contacting the catheter 10 can be configured to increase a retention force on the catheter 10 and reduce slippage due to creep and/or cyclic loading. As shown in FIG. 48, the surface 1300 can include stress risers 1304, which can be molded therein for example. The stress risers 1304 can take any suitable form, such as a abraided sections, rough sections, spiked sections, a diamond thread pattern, or overmolding a relatively softer material on top of a relatively harder material. The stress risers 1304 can produce gradients in the pressure applied to the catheter 10, such that the catheter 10 can be loaded into the shape shown in FIG. 48 (or similar shapes). This configuration results in a higher normal force to resist movement of the catheter 10 and minimizes minor slippage due to additional force being required for the catheter 10 to reflect around stress risers 1304.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples without departing from the scope of the claims.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A fixation device for a catheter, the fixation device comprising:
   a body defining a bore for reception of a catheter, the bore extending along a longitudinal axis;
   a first body portion of the body having a first bore portion; and
   a second body portion of the body having a second bore portion, the first and second body portions movable with respect to one another from an open configuration allowing the catheter to be side loaded at least partially into the bore and a closed configuration with the first and second portions secured together to thereby enclose a length of the catheter within the bore;
   wherein the first body portion includes a backstop protrusion extending toward the second body portion adjacent to the first bore portion; and the second body portion includes a backstop protrusion extending toward the first body portion adjacent to the second bore portion, the backstop protrusions of the first and second body portions at least partially overlapping along the longitudinal axis in the open configuration to provide a backstop for side loading of the catheter at least partially into the bore.

2. The fixation device of claim 1, wherein the body further defines one or more suture openings extending therethrough, the one or more suture opening configured to receive sutures to secure the body to tissue.

3. The fixation device of claim 1, wherein the body comprises one or more wings extending outwardly from the bore.

4. The fixation device of claim 1, further comprising a snap fit connector configured to hold the first body portion and the second body portion in the closed configuration.

5. The fixation device of claim 4, wherein the snap fit connector comprises a dual stage snap fit connector with a first stage allowing the catheter to be movable within the bore and a second stage retaining the length of the catheter within the bore.

6. The fixation device of claim 1, wherein the first body portion and the second body portion are configured to press-fit together in the closed configuration.

7. The fixation device of claim 1, wherein the first body portion and the second body portion are pivotably coupled together by a hinge.

8. The fixation device of claim 7, wherein the backstop protrusions of the first and second body portions and the hinge are disposed on the same side of the body relative to the bore.

9. The fixation device of claim 1, wherein the first bore portion comprises a recess defined in the first body portion; and the second bore portion comprises a projection of the second body portion configured to be inserted into the recess in the closed configuration to form the bore.

10. The fixation device of claim 1, wherein the backstop protrusions of the first and second body portions include stops that engage one another to restrict pivoting of the first and second body portions away from one another past the open configuration.

11. The fixation device of claim 1, wherein the first body portion and the second body portion comprise separate components.

12. The fixation device of claim 1, wherein the bore includes one or more ribs that extend radially therein to clamp on the catheter.

* * * * *